(12) United States Patent
Lee et al.

(10) Patent No.: US 10,005,677 B2
(45) Date of Patent: Jun. 26, 2018

(54) MICROPARTICLES AND A SYSTEM AND METHOD FOR THE SYNTHESIS OF MICROPARTICLES

(71) Applicant: University College Dublin, National University of Ireland, Dublin, Dublin (IE)

(72) Inventors: Gil Lee, Dublin (IE); Mark Platt, Loughborough Leicestershire (GB); James O'Mahony, Dublin (IE)

(73) Assignee: University College Dublin, National University of Ireland, Dublin, Dublin (IE)

( * ) Notice: Subject to any disclaimer, the term of this patent is extended or adjusted under 35 U.S.C. 154(b) by 650 days.

(21) Appl. No.: 14/404,575

(22) PCT Filed: May 31, 2013

(86) PCT No.: PCT/EP2013/061302
§ 371 (c)(1),
(2) Date: Nov. 28, 2014

(87) PCT Pub. No.: WO2013/178802
PCT Pub. Date: Dec. 5, 2013

(65) Prior Publication Data
US 2015/0183655 A1 Jul. 2, 2015

(30) Foreign Application Priority Data

May 31, 2012 (GB) .................................. 1209681.4

(51) Int. Cl.
| | | |
|---|---|---|
| *A61K 9/51* | (2006.01) | |
| *C01G 49/02* | (2006.01) | |
| *A61K 9/50* | (2006.01) | |
| *B01J 13/04* | (2006.01) | |
| *B01J 13/12* | (2006.01) | |
| *H01F 1/00* | (2006.01) | |
| *B01F 3/08* | (2006.01) | |
| *B01F 3/22* | (2006.01) | |
| *B01F 7/00* | (2006.01) | |
| *B01F 15/02* | (2006.01) | |
| *A61B 5/055* | (2006.01) | |
| *B01F 15/06* | (2006.01) | |

(52) U.S. Cl.
CPC ............ *C01G 49/02* (2013.01); *A61K 9/5094* (2013.01); *B01F 3/0811* (2013.01); *B01F 3/0853* (2013.01); *B01F 3/223* (2013.01); *B01F 7/00* (2013.01); *B01F 15/0203* (2013.01); *B01J 13/043* (2013.01); *B01J 13/125* (2013.01); *H01F 1/0054* (2013.01); *A61B 5/055* (2013.01); *B01F 2015/062* (2013.01); *C01P 2004/61* (2013.01); *C01P 2006/42* (2013.01)

(58) Field of Classification Search
CPC ...... A61K 9/107; A61K 9/1075; A61K 9/113; A61K 9/14; A61K 9/16; A61K 9/1682; A61K 9/1694
See application file for complete search history.

(56) References Cited

U.S. PATENT DOCUMENTS

| | | | |
|---|---|---|---|
| 2007/0172426 A1* | 7/2007 | Lee .................... | A61K 41/0028 424/9.32 |
| 2009/0311295 A1 | 12/2009 | Mathiowitz et al. | |
| 2011/0204533 A1 | 8/2011 | Winchester et al. | |

FOREIGN PATENT DOCUMENTS

| | | |
|---|---|---|
| WO | 2008048271 A2 | 4/2008 |
| WO | 2008054874 A2 | 5/2008 |
| WO | 2011087689 A2 | 7/2011 |

OTHER PUBLICATIONS

Combined Search and Examination Report under Sections 17 and 18(3), Intellectual Property Office, Great Britain Application No. GB1209681.4, dated Jan. 3, 2013, 8 pages.
International Searching Authority, United States Patent and Trademark Office, Partial International Search for PCT/EP2013/061302, dated Oct. 29, 2013, 7 pages.
International Searching Authority, United States Patent and Trademark Office, Search Report and Written Opinion for PCT/EP2013/061302, dated Jan. 10, 2014, 19 pages.
International Searching Authority, United States Patent and Trademark Office, International Preliminary Report on Patentability and Written Opinion for PCT/EP2013/061302, dated Dec. 11, 2014, 14 pages.

* cited by examiner

*Primary Examiner* — Micah Paul Young
(74) *Attorney, Agent, or Firm* — Holzer Patel Drennan

(57) ABSTRACT

There is provided a method of producing microparticles using an emulsion based synthesis route including: Providing a first fluid phase and a second fluid phase, wherein the first fluid phase is a continuous phase and the second fluid phase is a dispersed phase comprising a dispersed material, wherein the continuous phase is immiscible with the dispersed phase; Mixing the first continuous phase and the second dispersed phase in the presence of a surfactant in a shear device to form an emulsion of droplets of controllable size and having a narrow drop size distribution; Drying the emulsion to form microparticles of controllable size and having narrow size distribution, and wherein the microparticles may comprise spherical, crumpled, dimpled, porous or hollow microparticles morphology. Also provided is a system including shear device and drying arrangement. Also provided are micro particles of controllable size and morphology formed by the method.

15 Claims, 19 Drawing Sheets

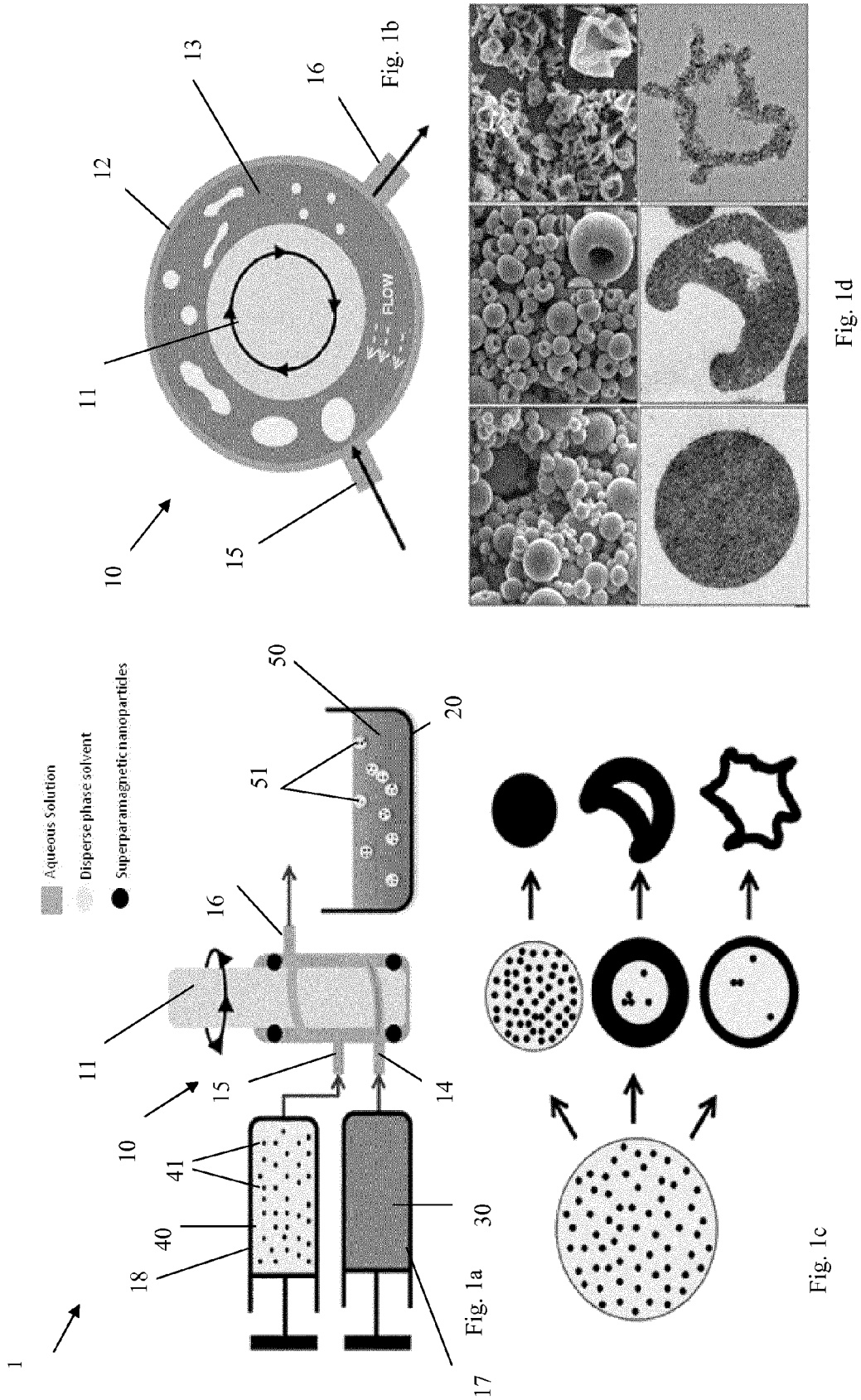

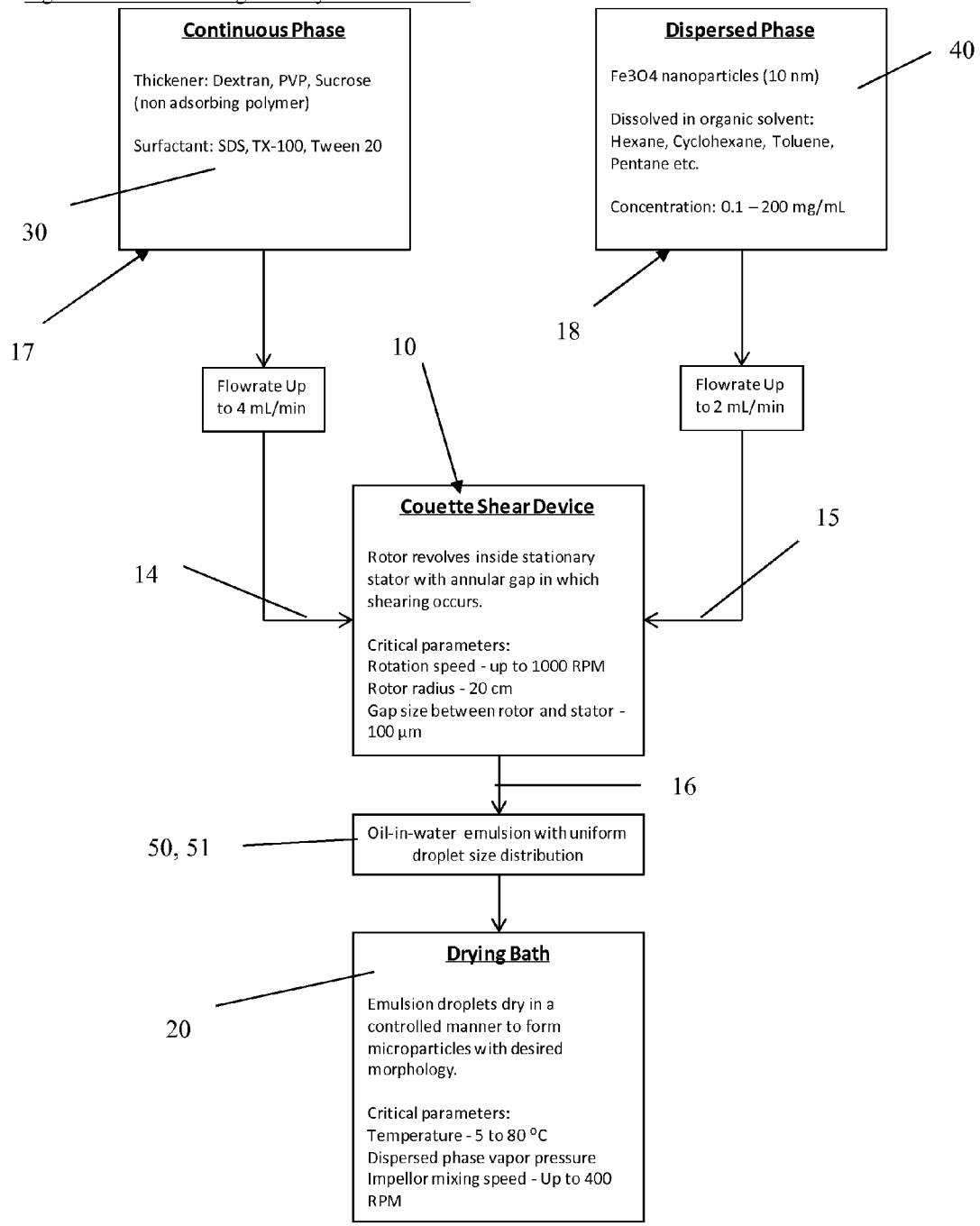

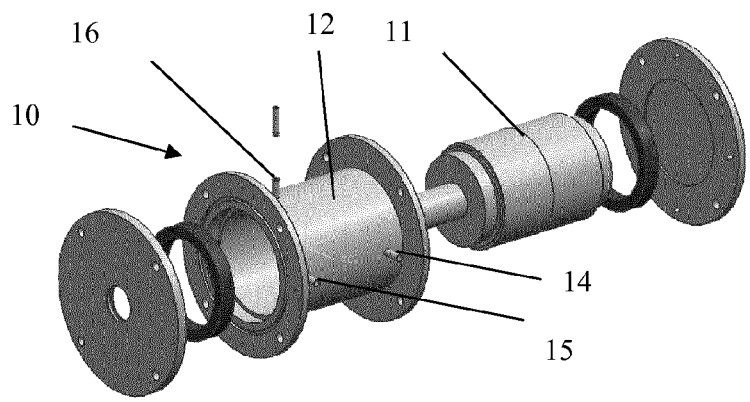
*Figure 3A Shear device showing bearings (black) to maintain consistent gap size.*
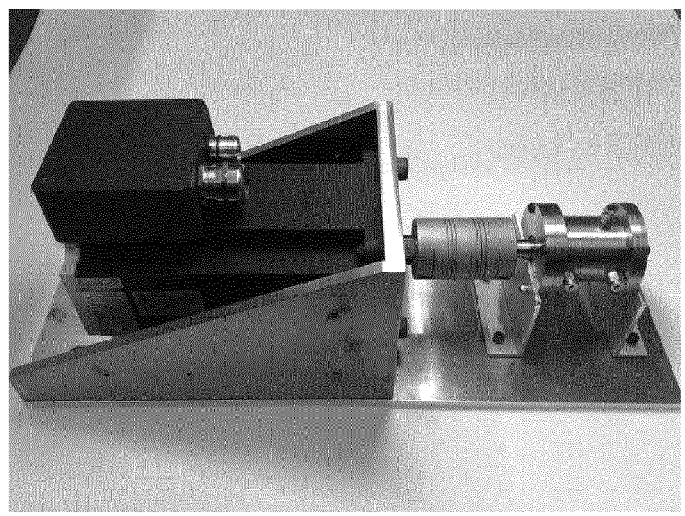
Figure 3b photograph of shear device system layout with motor and coupling.
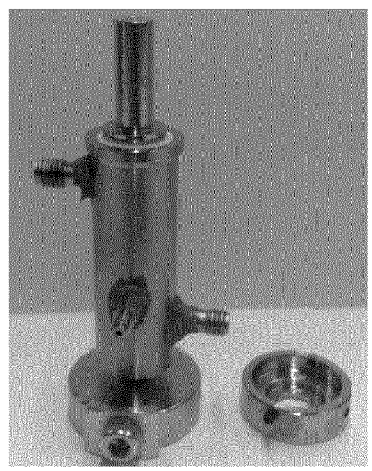
Figure 3c

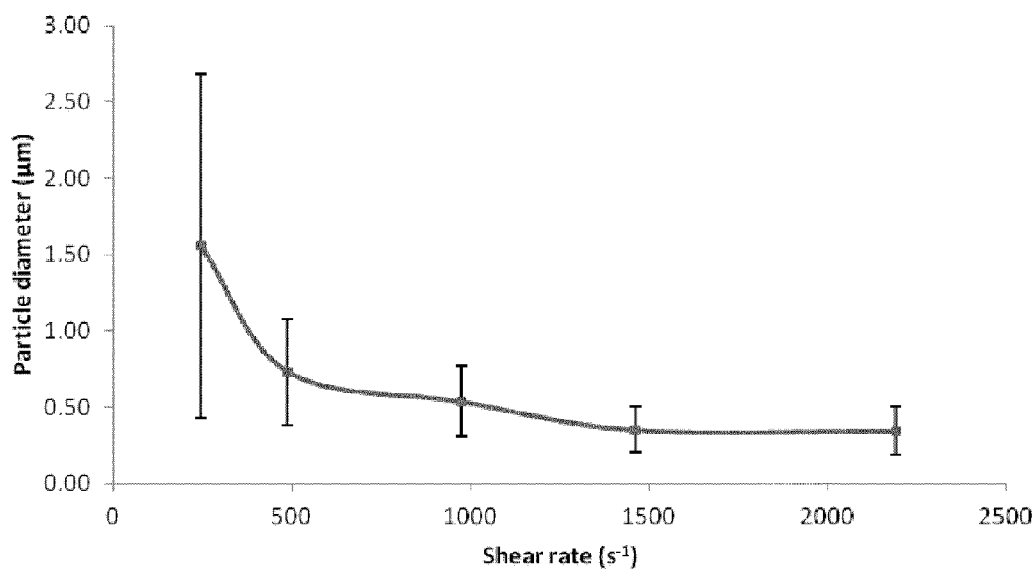
Figure 4 SMP sizes at different shear rates with error bars showing standard deviation. Cont. phase Dextran 25% w/w, 1% SDS w/w, disp. phase conc. 15 mg/ml. Φ 30%

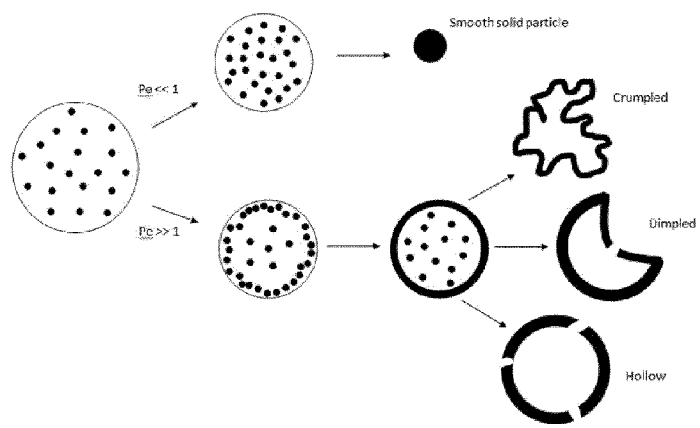
Fig. 7 is an illustration of a drying step according to the present application which is controllable to form particles of different morphologies.
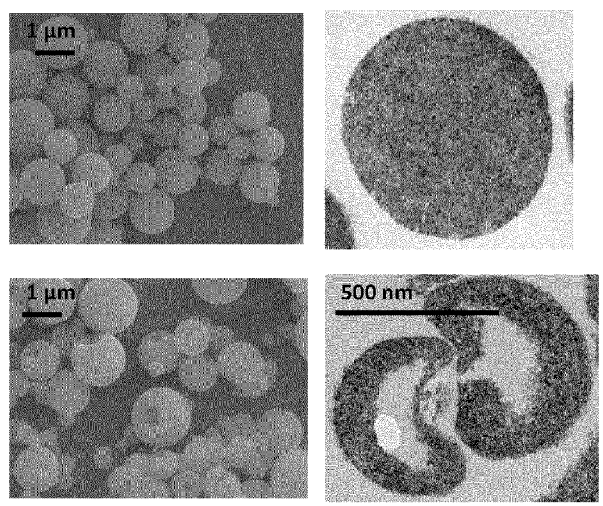
Figures 8 are images showing details of spherical, dimpled and crumpled particles.

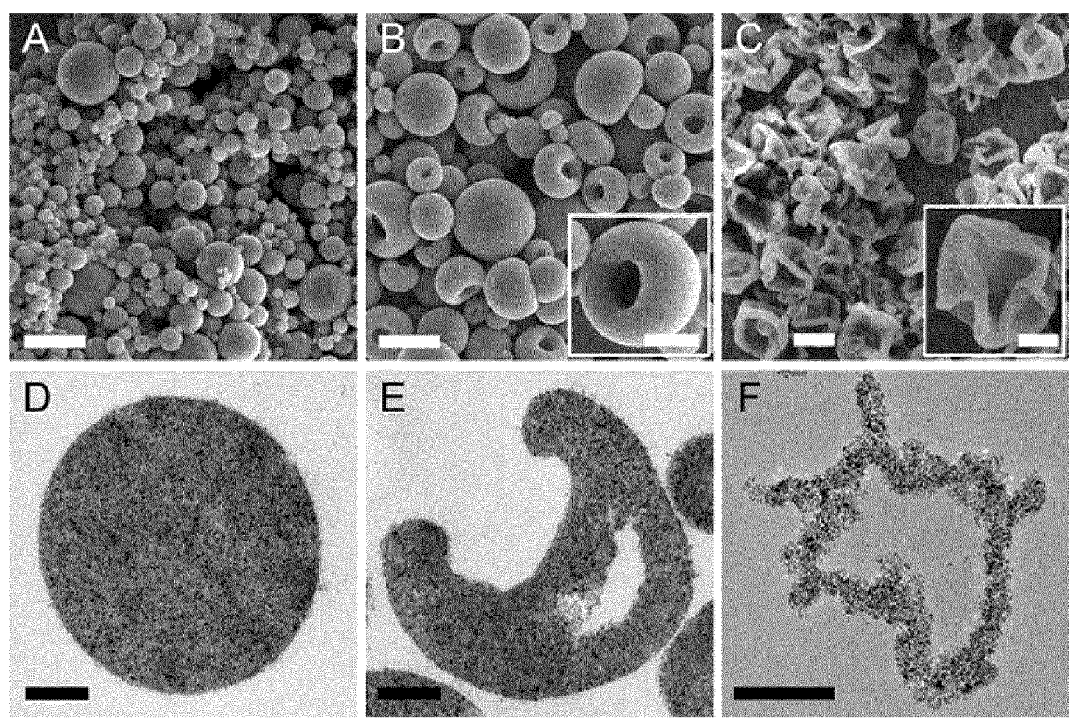
Figs 9 A- F

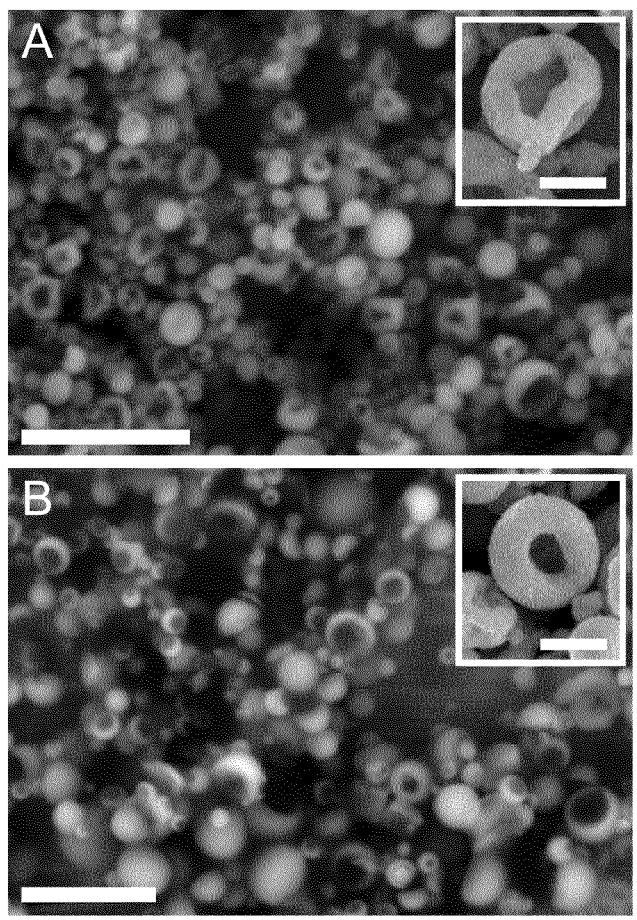
Figs. 14 A and 14 B

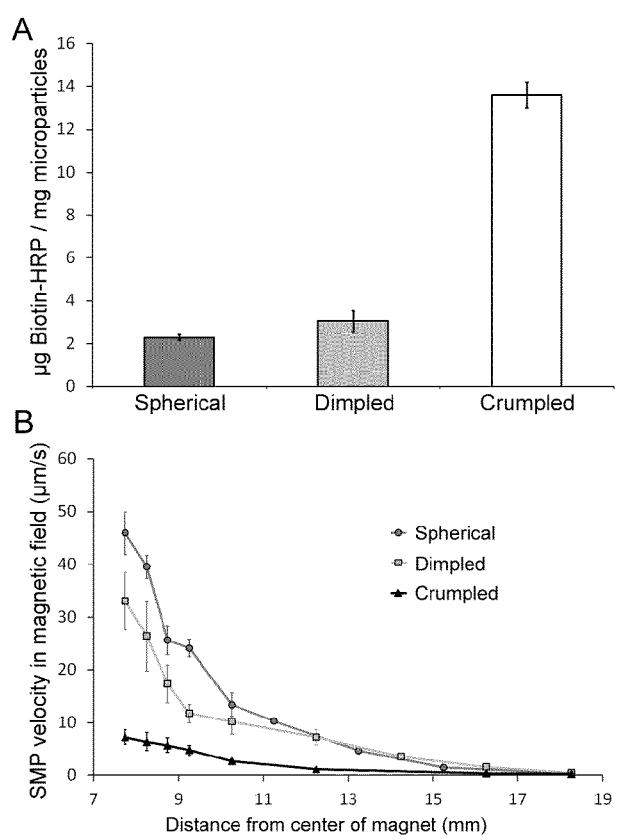
Figs 15 A and 15 B

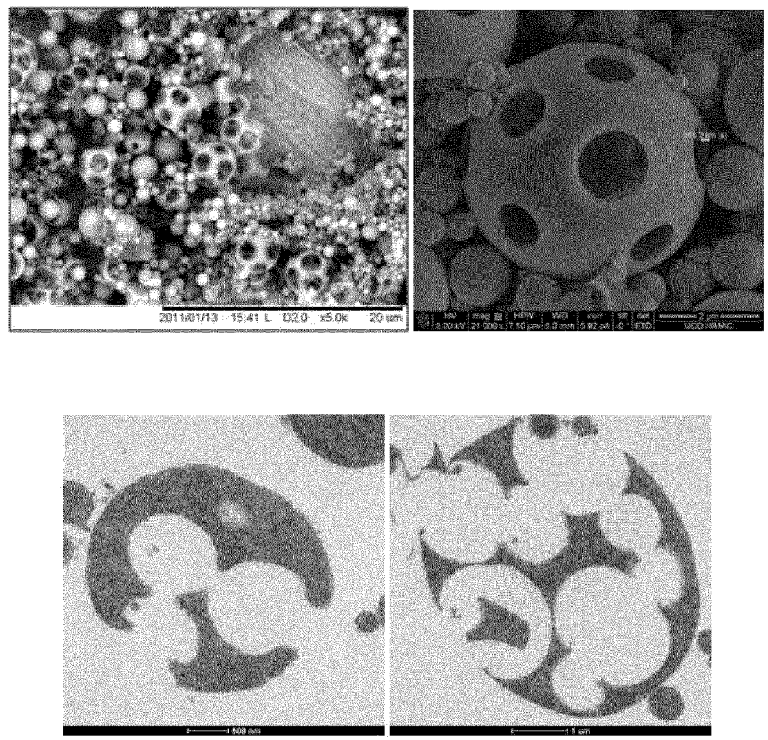

Figures 16: Top left - SEM image of batch of hollow microspheres with smaller dense microspheres. Top right - High Res SEM Image of hollow microsphere. Bottom right and left - TEM images of 80 nm thick cross sections of hollow microspheres showing internal structure.

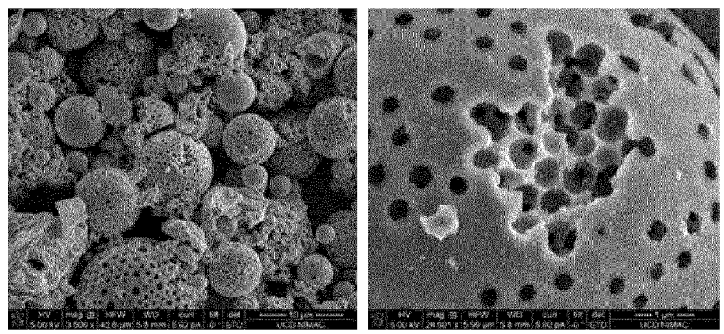

Figures 17: Left - High Res SEM image of batch of porous microspheres. Right - High Res SEM image of porous microsphere showing internal structure Figures 18 images of other observed SMP morphologies
- Porous with large internal void spaces
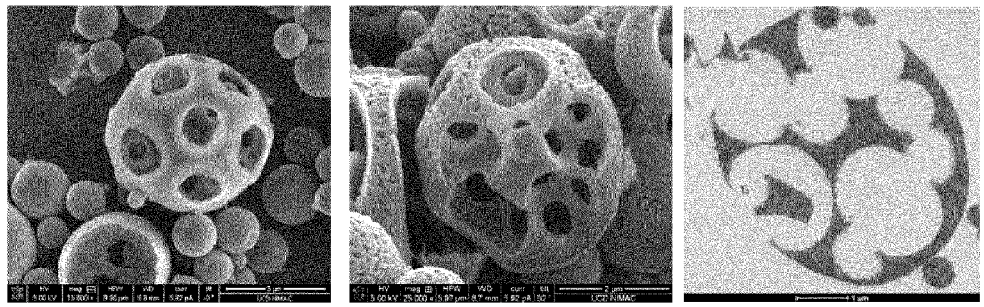
- Porous with small internal void spaces
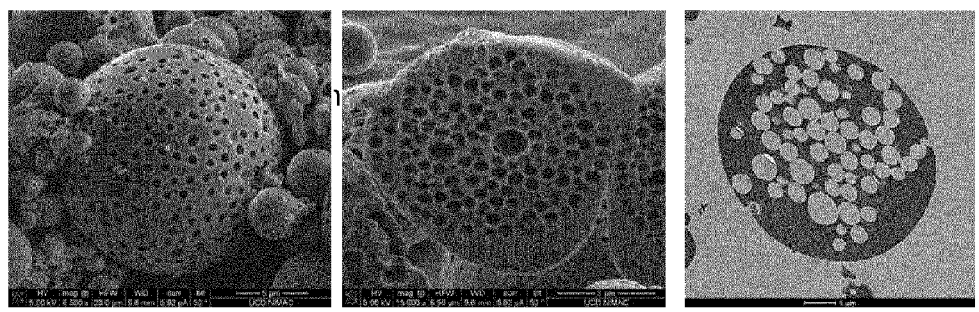

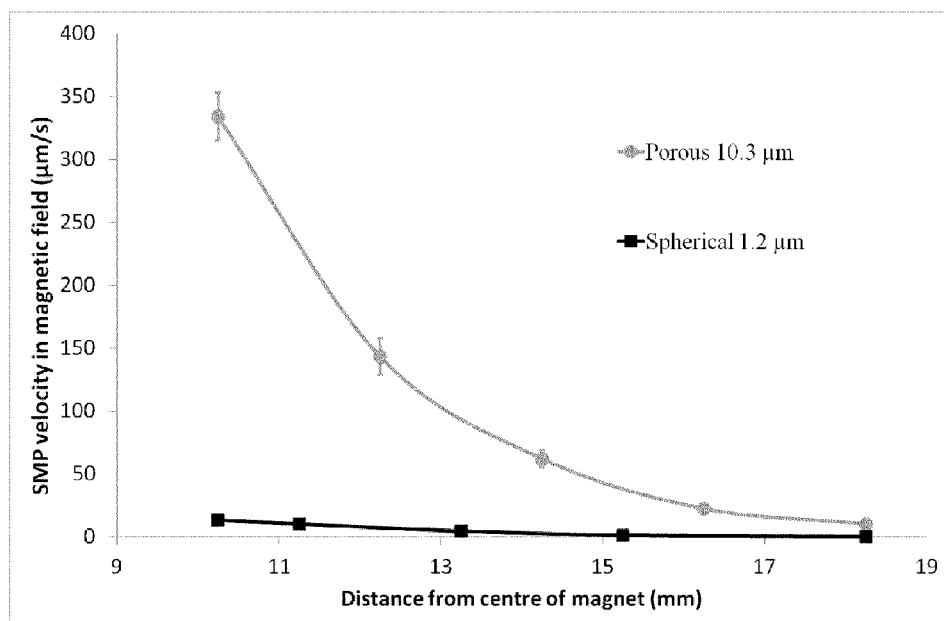
Figure 19: Magnetic mobility of Porous SMPs with diameter 10.3 ± 1.5 µm compared with spherical SMPs with diameter 1.2 ± 0.1 µm with distance from a fixed magnetic field source. The velocity of the Porous SMPs is 23.2 times larger than that of spherical SMPs, at equivalent distances from the magnet. Error bars represent standard deviation.

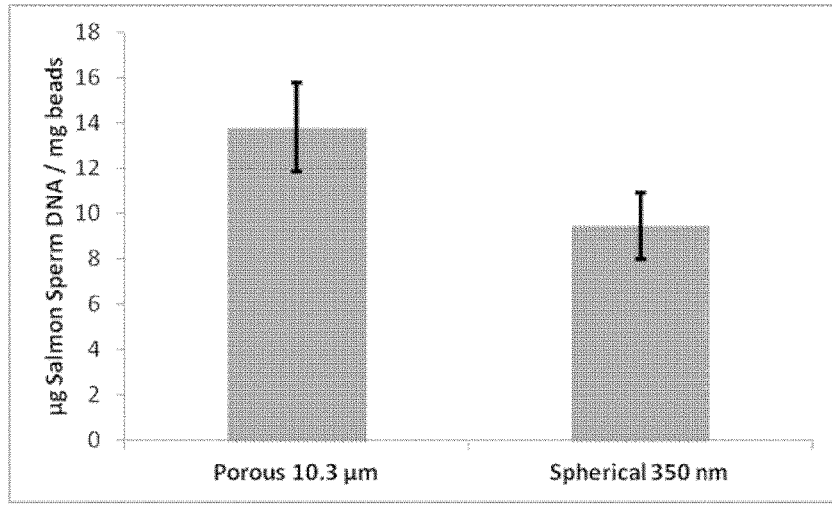

Figure 20: Salmon Sperm DNA binding capacity of silica coated SMPs. Porous SMPs with diameter 10.3 ± 1.5 µm and spherical SMPs with diameter 354 ± 49 nm were silica coated, and added to Salmon Sperm DNA in Guanidine Hydrochloride for 10 hours on a rotating wheel at RT. The change in concentration of the DNA in solution after removal of the microparticles was measured using a Cary Win UV Spectrophotometer to determine the binding capacity of the beads.

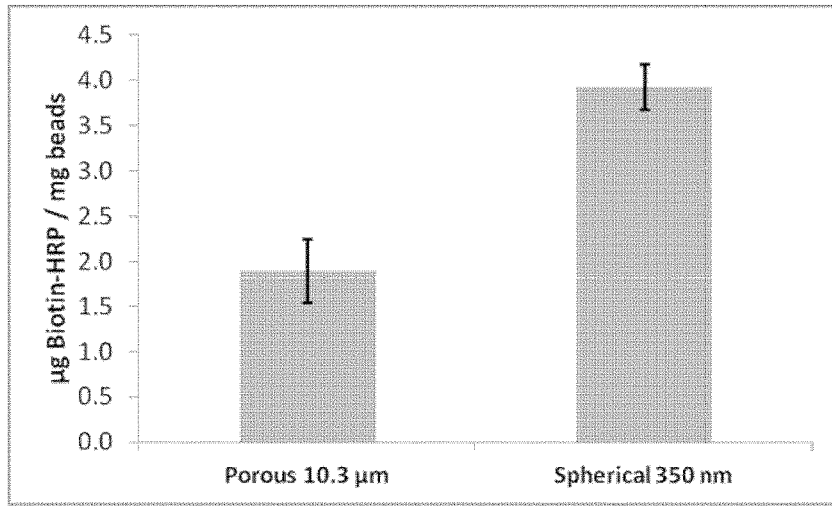

Figure 21: Biotin-HRP binding capacity of avidin-functionalized SMPs with porous and spherical morphologies. Porous SMPs with diameter 10.3 ± 1.5 µm and spherical SMPs with diameter 354 ± 49 nm were avidin functionalised and added to a solution containing Biotin-HRP 30 minutes on a rotating wheel at RT. Error bars represent standard deviation.

MICROPARTICLES AND A SYSTEM AND METHOD FOR THE SYNTHESIS OF MICROPARTICLES

PRIORITY CLAIM

The present application is a U.S. 371 National Phase Patent Application and claims benefit of Patent Cooperation Treaty application No. PCT/EP2013/061302, entitled "MICROPARTICLES AND SYSTEM AND METHOD FOR THE SYNTHESIS OF MICROPARTICLES" and filed on 31 May 2013, which takes priority from U.K. Patent Application 1209681.4 filed on 31 May 2012, all of which are incorporated herein by reference in their entirety.

FIELD

Background

Superparamagnetic microparticles (SMPs) have been widely used for bioseparation applications, for example, in point of care testing, diagnostics, and high through screening, due to the speed, ease, efficiency, and cost effective nature of magnetic separation. These particles are used in a number of biomedical applications, for example, in vivo imaging with magnetic resonance imaging and targeted drug delivery, due to their response to electromagnetic radiation. These micro-particles are normally coated with a polymer that stabilizes them in aqueous solution and provides chemical groups to which biomolecules, such as, DNA and proteins can be conjugated. Commercially available SMPs, defined as particles over 30 nm in diameter, are typically spherical and composed of an assembly of, for example, metal oxide superparamagnetic nanoparticles.

In previous approaches, the nanoparticles have been distributed in a polymer microparticle matrix or self-assembled to form a tightly packed spherical SMP without the addition of a polymer component. An emulsification method may be used for example often a crude emulsion was first prepared by manually stirring the two phases together and then pumped into a mixing device. Fragmentation of the crude emulsions took place within the device and the homogenized emulsion emanated through an outlet port. This emulsion synthesis method can be problematic due to the inconsistencies in the premixing step potentially leading to the formation of very small droplets and limited throughput time due to the phase separation of the metastable premixed emulsions. As soon as a premixed emulsion is produced the phases begin to separate and separation becomes significant after 20-30 minutes limiting the batch production time to this duration. Separation further results in the variation of droplet size and uniformity over the course of the synthesis. Accordingly, there are problems with current methods and systems for production of microparticles. There is therefore a need for an improved system method for producing microparticles, in particular superparamagnetic microparticles.

More complex SPM structures have also been produced. In another approach, hollow SMPs consisting of iron oxide nanoparticles embedded in polystyrene have been fabricated using, for example, an inverse microemulsion polymerization process. The surfaces of the nanoparticles have been made amphiphilic through functionalization with both active hydrophilic hydroxyl groups and hydrophobic oleic ester groups. The amphiphilic nanoparticles could then be used as colloidal stabilizers for inverse water-in-oil emulsions and also mediated the polymerization of styrene monomers in the oil phase at the droplet interface to form a hollow polystyrene iron oxide composite SMP up to a couple of micrometers in diameter. In another approach, hollow and porous $Gd_2O_3$ microspheres have been synthesized through the deposition of superparamagnetic material together with a polymer on the surface of or within a spherical gelatin template, which was later removed using calcination leaving behind a hollow or porous SMP roughly 100 or 200 nm in diameter, respectively. In a further approach, polymer-iron oxide composite SMPs have been synthesized using water-oil-water double emulsions in which the middle oil phase consists of a mixture of both a liquid pre-polymer and superparamagnetic nanoparticles. After UV curing and drying of the internal water phase, polymer magnetite iron oxide SMPs with a hollow hemispherical morphology 12 μm in diameter were formed. These methods for the production of SMPs involve a large number of steps such as the removal of a sacrificial template on which the superparamagnetic material has been deposited or incorporate a polymeric material, which often reduces the magnetic moment of the resulting SMPs.

The present specification provides an improved method and system for producing microparticles and superparamagnetic microparticles that aims to address problems including the above noted problems with existing methods and systems for producing microparticles. The system and method of the present specification provide for scalable production. The system and method also provide for improved uniformity of microparticle size and control of size and type of microparticle.

The present specification also provides improved microparticles having controllable size and morphology. The method and system described provide production of particles having high surface area to volume ratio and therefore high binding capacity. A process is described that results in a highly simplified production of the magnetic particles resulting in a decreased cost of production. The present specification also provides a method for producing magnetic particles of tuneable magnetisation and, for example, having high magnetic mobility.

STATEMENTS OF INVENTION

According to the present specification there is provided a method in accordance with claim 1 of producing microparticles (100) using an emulsion based synthesis route including:

(i) Providing a first fluid phase and a second fluid phase, wherein the first fluid phase is a continuous phase (30) and the second fluid phase is a dispersed phase (40) comprising a dispersed material (41), wherein the continuous phase is immiscible with the dispersed phase, (ii) Mixing the first continuous phase and the second dispersed phase in the presence of a surfactant in a shear device (10) to form an emulsion (50) of droplets (51) of controllable size and having a narrow drop size distribution, (iii) Drying the emulsion to form microparticles (100) of controllable size and having narrow size distribution, and wherein the microparticles may comprise spherical, crumpled, dimpled, porous or hollow microparticles morphology.

Optional features are provided in accordance with the dependent claims 2 to 62. The droplets may be less than 50 micron diameter and the microparticles formed of less than 15 micron diameter. The microparticles formed have a narrow size distribution having a % CV diameter of the order of 25% CV or less. In one arrangement, the method further comprising: Controlling microparticle morphology to provide microparticles of spherical, crumpled, dimpled, porous or hollow morphology. In one arrangement, the method further comprising: Controlling size and uniformity of size distribution of the emulsion droplets to control size and uniformity of size distribution of microparticles. Droplet size may be <20 microns diameter. Microparticle size is in the range of 100 nm-1 micron, most preferably 200 nm-1 micron. In one arrangement, the method further comprising: Providing a shear device (10) having separate first and second inlets for the first continuous phase and the second dispersed phase. The mixing step may comprise an emulsifying step wherein the second dispersed phase is emulsified into the first continuous fluid phase in the shear device. The emulsifying step may occurs upon entry of the first and second phases to the shear device, and the dispersed phase is emulsified into the continuous phase to form the emulsion. The dispersed material may comprise nanoparticles. The dispersed material may comprise superparamagnetic nanoparticles. The nanoparticles may be metal oxide or iron nanoparticles, most preferably iron oxide nanoparticles, for example, $Fe_2O_3$ and/or $Fe_3O_4$. The nanoparticles may be Ni or PtFe nanoparticles. In one arrangement, the method further comprising further comprising: controlling of magnetisation of the microparticles. Magnetisation of microparticles may be controlled by controlling the concentration of iron oxide $Fe_2O_3$ and/or $Fe_3O_4$ nanoparticles in the dispersed phase in the range of 0.1-200 mg/mL. The magnetisation of the microparticles is controllable substantially in the range of 20-110 emU/g, or preferably 20-100 emU/g.

In one approach controlling size and uniformity of size distribution of the emulsion droplets to control size and uniformity of size distribution of microparticles may comprise controlling the shear device to control droplet size and uniformity of size distribution and controlling selection of continuous and dispersed phases. In one approach the method may include controlling: the shear rate and/or dispersed phase volume fraction and/or continuous phase viscosity and/or surfactant concentration and/or the viscosity ratio between phases, and/or the dispersed phase viscosity, to control microparticle size and uniformity of the size distribution of the microparticles. The shear rate may be controlled wherein the shear device is operable at rotation rates up to 2000 rpm, preferably at rates between 50 and 1000 or 50 and 1500 rpm as required. In one approach the method may include controlling viscosity ratio between phases dispersed to continuous in the range between 0.01 and 1, most preferably substantially 0.1. In one approach the method may include controlling the dispersed phase volume fraction in the range of 30-90% as required, by controlling the relative flow rates of the first continuous and second dispersed phases into the shear device.

Controlling microparticle morphology to form microparticles of different morphology may comprise controlling parameters of the method including: nanoparticle concentration and/or surface chemistry, and/or the rate of drying the emulsion. The method may comprise controlling drying to control the microparticle morphology. Preferably, the crumpled, dimpled, and porous microparticles have a high surface area to volume ratio in comparison with spherical particles of similar volume. The microparticles may be comprised of superparamagnetic microparticles formed through emulsion templated self-assembly of superparamagnetic nanoparticles. The microparticles may comprise aggregated nanoparticles. Preferably the crumpled, dimpled and porous microparticles have a high binding capacity relative to spherical microparticles of similar diameter or volume. Preferably, the dimpled and crumpled microparticles having a surface area to volume ratio 6-7 time greater than the surface area to volume ratio of a spherical microparticle of similar volume. Preferably, the crumpled microparticles have a binding capacity 6-7 times greater than that of spherical microparticle of similar volume. Preferably, the crumpled microparticles have a magnetic mobility substantially 6 times greater than that of spherical microparticles of similar volume.

In one arrangement, the method comprising an emulsion templated self-assembly method. In one arrangement, the method comprising a continuous method for producing microparticles. Preferably, the method being configured to provide a high throughput production of emulsion wherein control of the first and second phases and/or the mixing and the drying steps enables reproducible synthesis of uniformly sized microparticles having a required morphology on a large scale. In one arrangement, the first fluid phase is a continuous aqueous or oil phase immiscible with the second dispersed phase. The continuous phase may comprise the surfactant and the surfactant type and concentration are selected and controlled as required. The first continuous phase may comprise a thickener wherein the thickener type and concentration are selected and controlled as required to control the viscosity of the continuous phase. The dispersed phase may comprise an organic solvent. The dispersed material may comprise nanoparticles or a nanoparticle suspension. The dispersed material may comprise a polymer or a polymer solution. The dispersed phase may comprise nanoparticles having a particle diameter of between 3 and 30 nm. In one arrangement the method comprises varying the concentration of the dispersed material in the dispersed phase to control microparticle size and morphology. The concentration of the dispersed nanoparticles in the dispersed phase is preferably in the range of 0.1-0.5 mg/ml for forming crumpled and dimpled microparticles. The dispersed material may comprise iron oxide nanoparticles and the concentration of iron oxide nanoparticles in the dispersed phase was varied between 0.1 and 200 mg/ml to control microparticle morphology wherein at or above 1 mg/ml the microparticles were smooth and spherical, at 0.5 mg/ml the microparticles were dimpled and at 0.1 mg/ml the microparticles had a crumpled morphology. The dispersed material may comprise iron oxide nanoparticles and the surface chemistry of the nanoparticles is varied to provide microparticles of the required morphology. The surface chemistry of oleic acid ligands on the surface of the nanoparticles may be controlled to produce microparticles of crumpled morphology. The emulsion templated synthesis route may comprise an oil in water or water in oil templated based synthesis route. In one approach the method may include controlling temperature in the shear device and the drying bath and selection of solvent of the dispersed phase as required to control the dispersed phase evaporation rate. The shear device may comprise a device having a rotor configured to revolve inside a stationary stator and an annular gap provided between the rotor and stator in which emulsification occurs, the shear device comprising first and second inlet ports wherein the first continuous phase and the second dispersed phase are provided to the shear device via separate inlet ports. In one approach the method may include controlling the dispersed phase volume fraction during the mixing step by the control of the flow rate at the separate inlet ports to the shear device for the continuous phase and the dispersed phase. The second dispersed phase may be provided into the first continuous phase in the shear device. The method may comprise controlling the rotor speed and/or controlling the gap size between the rotor and stator to optimise the gap size and/or controlling operation of the shear device to control the rotation of the rotor in the shear device and/or controlling the flow rate of the continuous and dispersed phases to the shear device and/or controlling the viscosity ratio between the continuous and dispersed phases. The drying of the emulsion droplets may be controlled to control microparticle morphology. Drying of the emulsion may be controlled to control the surface area and volume ratios of the particles. In one approach the method may include providing a drying bath for drying of the emulsion. The drying bath may comprise an enclosed drying bath with heating means and an impellor for agitating the emulsion. The method may comprise controlling drying including drying rate by controlling temperature and/or emulsion mixing and/or the dispersed phase vapour pressure. The temperature may be varied substantially between 5 and 80 degrees Celsius. In one approach the method may include controlling emulsion mixing in the drying bath by controlling operation of the use of an impellor wherein the impellor mixing speed is varied as required. In one approach the method may include controlling diffusion of the dispersed phase in the continuous phase.

The specification also provides in another arrangement microparticles provided by the method described in accordance with claim 63. Further optional features are provided in claims 64 to 72. Microparticles produced by the method described, comprising spherical or crumpled or dimpled or porous or hollow microparticles wherein the microparticles are of substantially uniform size or have a relatively uniform size distribution. Microparticles may comprise a high surface area per unit volume. The microparticles may have a high binding capacity. The microparticles may comprise superparamagnetic microparticles. The microparticles may having a high magnetic mobility. Preferably the microparticles are of controllable size and morphology. Preferably, the dimpled and crumpled microparticle morphologies demonstrate a higher surface area to volume ratio than similar sized spherical microparticles. The microparticles may comprise iron oxide microparticles wherein the use of iron oxide nanoparticles enables production of microparticles with a tuneable magnetisation and relatively high mobility.

Also provided are superparamagnetic microparticles of claims 73 to 84 having a high surface area per unit volume and high magnetic mobility, the microparticles comprising spherical or dimpled or crumpled or porous or hollow microparticles. The superparamagnetic microparticles preferably having controllable size and morphology. The microparticles may comprise crumpled particles having a binding capacity per unit volume 6-7 times higher than spherical microparticles of equivalent diameter. The microparticles have a magnetic mobility substantially equivalent to the separation velocity of spherical particles of similar diameter and surface area per unit volume higher than that of a spherical particle of equivalent diameter. The surface area per unit volume may be of the order of 6-7 times greater than that of a spherical particle of equivalent diameter. The microparticles may be comprised of iron oxide for example comprise $Fe_3O_4$ and/or $Fe_2O_3$ nanoparticles. The microparticles may have a high magnetic moment. Preferably the microparticles are characterised in that the particles have a high surface area and magnetic mobility. Preferably, superparamagnetic comprising iron oxide microparticles have a higher mobility than polymer-iron oxide composite particles of similar size or morphology. Preferably, the iron oxide nanoparticles self-assemble upon drying.

Also provided are a shear mixing device of claim 85 and dependent claims 86 to 88 for mixing a first fluid phase and a second fluid phase comprising: first and second inlet ports for a first fluid phase and a second fluid phase respectively, the first and second inlet ports being configured for connection to continuous and dispersed phase reservoirs
    a rotor configured to rotate inside a stationary stator, the rotor and stator being arranged such that a gap is provided therebetween and such that in use as the rotor rotates emulsification of the dispersed phase into the continuous phase occurs inside the shear device in said gap to form an emulsion comprising emulsion droplets, wherein the radius of the rotor and gap size between the rotor and stator are optimised to minimise emulsion droplet size distribution, and
    further comprising flow rate control means for controlling the flow rate of the continuous phase and the flow rate of the dispersed phase into the shear device, and shear control means for controlling the shear rate and/or rotation of the rotor.

Preferably the device having control means for controlling the dispersed phase volume fraction by controlling the relative flow rates of the first continuous and second dispersed phases into the shear device. Preferably, the gap size being substantially 100 microns or 100 microns. Preferably, the rate of rotation of the rotor may be controlled in the range of substantially up to 2000 rpm.

Also provided is a drying bath of claim 89 and dependent claims 90 to 92 comprising an enclosed drying bath volume configured to provide for controlled drying of an emulsion to produce microparticles of different morphologies, the drying bath further comprising an agitation means, heating means, and control means for controlling the temperature and head space vapour pressure and the degree of mixing to achieve the required drying rate and required microparticle morphology.

Also provided is a system of claim 95 for the controlled production of microparticles comprising a shear device as described for producing an emulsion, connected to a drying bath as described and configured to dry the emulsion in a controlled manner to form microparticles.

The specification also provided a further a method of producing microparticles in accordance with claims 95 and 96 to 100 using an emulsion solvent evaporation method, comprising the steps of: preparing a primary emulsion, comprising,
emulsifying a polymer or nanoparticle suspension in a second immiscible phase evaporating the solvent to provide crystallisation/precipitation of the polymer or nanoparticles to form microparticles.
and
    A further method of producing microparticles using an emulsion solvent evaporation method, comprising the steps of:
preparing a primary emulsion
    in a first emulsifying step emulsifying a polymer or nanoparticle suspension in a second immiscible phase
    in a second step diluting the primary emulsion into a drying bath, evaporating the solvent to provide crystallisation/precipitation of the polymer or nanoparticles to form microparticles.

BRIEF DESCRIPTION OF THE DRAWINGS

FIG. 1A is a system diagram showing an embodiment of the system according to the present specification, the system including a shear mixing device having first and second inlets and an outlet to a drying device; FIG. 1B is a top plan view of the shear device of FIG. 1A; FIGS. 1C and 1D show illustrations and images of microparticles of different morphology formed using the system and method according to the present specification;

FIG. 2 is a system/method block diagram illustrating components of a device for producing microparticles according to the invention and showing the features that may be varied and controlled to control the output of microparticles according to a method of the present specification;

FIGS. 3A, 3B and 3C are photographs of a shear device of a system according to the present specification; the shear mixer shows individual inlets for aqueous and dispersed phases, and emulsion outlet on top. Teflon o-rings were used on the top and bottom of the rotor to seal the shearing area and prevent leakage, and to maintain the gap size between the rotor and stator.

FIG. 3E shows a Couette shear mixer showing individual inlets for aqueous and dispersed phases, with emulsion outlet on top right. Droplet size was adjusted through variation of the shear rate, γ', which for low dispersed phase volume fractions can be approximated as γ'=Riω/(Ro−Ri), where Ri is the inner rotor radius, Ro is the outer radius of the stator, and ω is the angular velocity of the rotor. Teflon O-rings were used to prevent leakage.

FIG. 4 is a graph illustrating SMP sizes at different shear rates with error bars showing standard deviation. Cont. phase Dextran 25% w/w, 1% SDS w/w, disp. phase conc. 15 mg/ml. Φ 30%.

FIG. 5c bottom shows SEM Image of microparticles settled to bottom of 800 mL drying bath, after removal of fine particles less than approximately 250 nm in the supernatant. Average microparticle size 354±49 nm measured using Dynamic light scattering.

FIG. 7 is a figurative illustration of a drying of a method according to the present specification which illustrates control of drying to control microparticle morphology.

FIG. 8 are images of particles of different microparticle morphologies obtained by a method according to the present specification;

FIGS. 9A-C shows a series of SEM images of SMPs produced with ferrofluid nanoparticle concentrations of (A) 1 g/L, (B) 0.5 g/L, and (C) 0.1 g/L, with insets in (B) and (C) showing magnified images. All other factors were kept constant. A transition from spherical to dimpled and crumpled microparticles occurs with decreasing nanoparticle concentration. Continuous phase dextran 25% w/w, SDS 2% w/w, flow rates of continuous and dispersed phases 0.75 and 0.25 mL/min, respectively. FIGS. 9D-F shows TEM images of cross sections of microparticles from (A), (B), and (C) and shown in (D), (E), and (F), respectively. Hollow areas inside the dimpled and crumpled particles suggest that during drying a nanoparticle shell first develops at the surface of the droplet and then collapses inward as drying continues. Scale bars=11 μm in (A-C) (500 nm in insets in (B) and (C)). Bars=250 nm in (D-F).

FIGS. 14A and 14B are SEM images of SMPs produced with ferrofluid nanoparticle concentrations of (A) 1 g/L and (B) 5 g/L, both washed twice with ethanol, with insets showing magnified images. Continuous phase dextran 25% w/w, SDS 2% w/w, flow rates of continuous and dispersed phases 0.75 and 0.25 mL/min, respectively. Microparticles produced with 1 g/L nanoparticle concentration show signs of crumpling, whereas the microparticles produced with 5 g/L nanoparticle concentration are dimpled. Scale bar=5 μm (1 μm in insets).

FIGS. 15 and 15B are graphs as follows: (A) Biotin-HRP binding capacity of avidin-functionalized SMPs with different morphologies. Carboxyl-functionalized spherical SMPs were used as a blank. The dimpled SMPs have slightly higher binding capacities (1.2×) than spherical SMPs, the crumpled microparticles have binding capacities 6-7 times higher than the spherical SMPs. Error bars represent standard deviation. (B) Velocity of SMPs of diameter 1.2±0.1 μm (largest cross-sectional diameter measured for dimpled and crumpled microparticles) with distance from a fixed magnetic field source. The velocities of dimpled and crumpled SMPs are 1.3 times and 6.2 times lower than the spherical SMPs, respectively. This can be attributed to the lower nanoparticle content per SMP due to the hollow cores of the dimpled and crumpled particles. Error bars represent standard deviation.

FIGS. 16 and 17 are images of other observed SMP morphologies. FIG. 16: Top left—SEM image of batch of hollow microspheres with smaller dense microspheres. Top right—High Res SEM Image of hollow microsphere. Bottom right and left—TEM images of 80 nm thick cross sections of hollow microspheres showing internal structure. FIG. 17: Left—High Res SEM image of batch of porous microspheres. Right—High Res SEM image of porous microsphere showing internal structure.

FIG. 18 are images of other observed SMP morphologies. upper line of images show porous microparticles with large internal void spaces lower line of images show porous microparticles with small internal void spaces.

FIG. 19 is a graph of Magnetic mobility of Porous SMPs with diameter 10.3±1.5 μm compared with spherical SMPs with diameter 1.2±0.1 μm with distance from a fixed magnetic field source. The velocity of the Porous SMPs is 23.2 times larger than that of spherical SMPs, at equivalent distances from the magnet. Error bars represent standard deviation.

FIG. 20 is a bar graph of Salmon Sperm DNA binding capacity of silica coated SMPs. Porous SMPs with diameter 10.3±1.5 μm and spherical SMPs with diameter 354±49 nm were silica coated, and added to Salmon Sperm DNA in Guanidine Hydrochloride for 10 hours on a rotating wheel at RT. The change in concentration of the DNA in solution after removal of the microparticles was measured using a Cary Win UV Spectrophotometer to determine the binding capacity of the beads.

FIG. 21 is a graph showing Biotin-HRP binding capacity of avidin-functionalized SMPs with porous and spherical morphologies. Porous SMPs with diameter 10.3±1.5 μm and spherical SMPs with diameter 354±49 nm were avidin functionalised and added to a solution containing Biotin-HRP 30 minutes on a rotating wheel at RT. Error bars represent standard deviation.

DETAILED DESCRIPTION

Figure 3D:
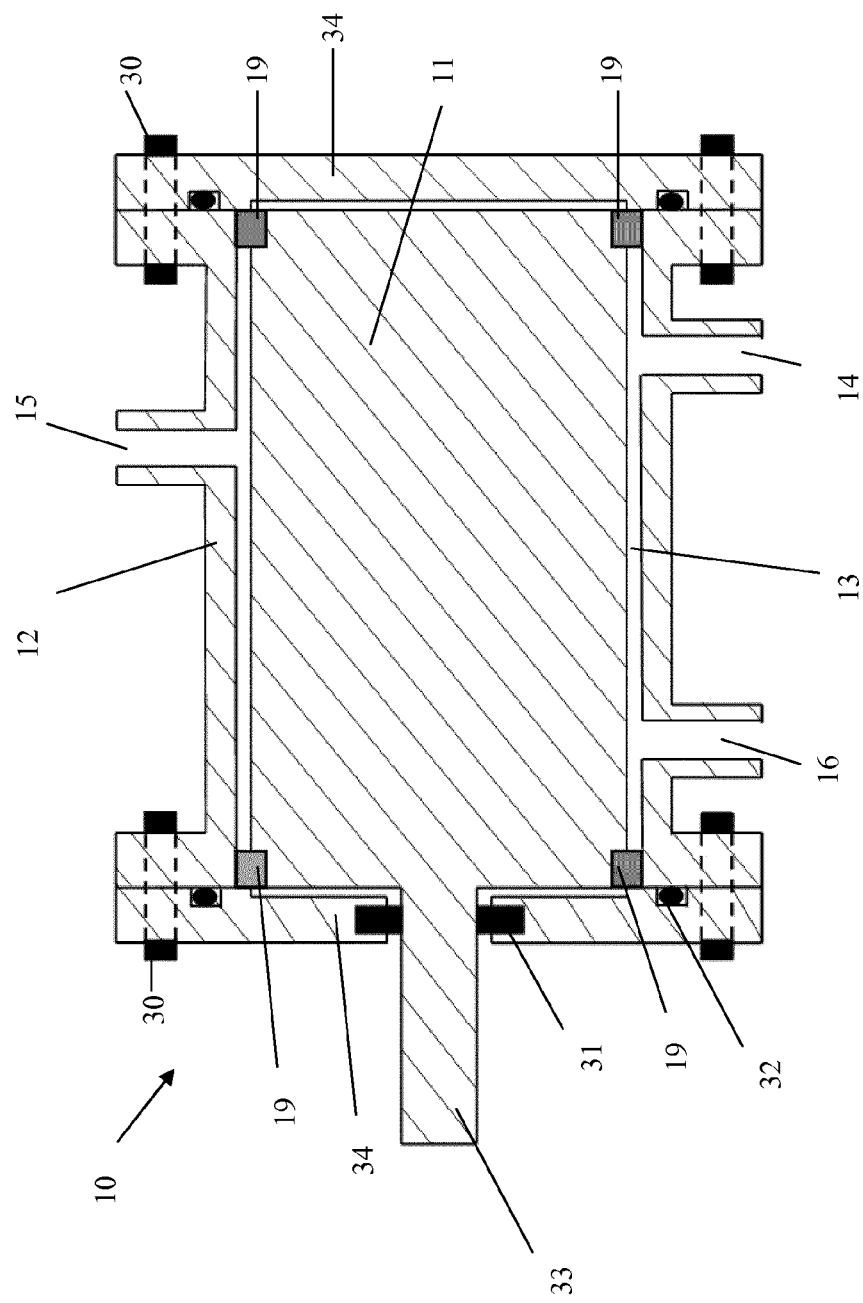
FIGS. 3D and 3E are diagrams of two alternative shear device arrangements of a system according to the present specification.

The present specification describes a system and method for the production of microparticles via emulsion based synthesis or emulsion template self assembly. The method addresses the above noted problems and provides an improved control over the steps of mixing and emulsification and drying to provide for the reproducible synthesis of microparticles with the desired size and morphology as required for different applications. The arrangement of system and the method provide for scalable production of microparticles. Further the system and method provide for the production of microparticles of improved uniformity of size and different morphologies.

According to the method of the present specification various alternative forms of microparticles have been produced including spherical microparticles and dimpled, crumpled porous and hollow microparticles. The method provides for production of particles of tuneable magnetisation. Accordingly, the method provides for production of particles for use in multiplex applications. The method provides for production of monodisperse particles, including microparticles having a coefficeint of variance (CV) of diameter of <25%. The method provides for production of microparticles of controlled morphology including dimpled and crumpled microparticles having magnetic velocities and surface area to volume ratios different from spherical microparticles of similar size. The method provides for production of microparticles of controlled morphology further including porous and hollow microparticles.

Referring to drawings FIGS. 1, 2 and 3 a system 1 and a method 200 according to an exemplary arrangement of the present specification for producing microparticles 100 are described.

Referring initially in particular to FIG. 1 and FIG. 3 the system 1 comprises a shear device 10 connected to a drying device 20. The shear device 10 comprises a housing having separate inlets 14 and 15 for a first fluid phase and a second fluid phase and an emulsion outlet 16. The inlets 14 and 15 are connected to first and second fluid phase reservoirs 17 and 18. The first fluid phase is a continuous phase 30 and the second fluid phase is a dispersed phase 40 which comprises a dispersed material 41. In the exemplary arrangement as illustrated, the dispersed material comprises a superparamagnetic material for example, superparamagnetic nanoparticles. An emulsion 50 is formed in the shear device 10 by mixing the continuous and dispersed phases 30 and 40. The emulsion 50 is provided via the emulsion outlet 16 to the drying device 20 for drying. The emulsion outlet 16 is located to the upper side of the shear device 10. It is significant that the emulsification occurs in the shear device as the first and second phases enter and are mixed therein.

The continuous phase 30 is an aqueous phase or oil phase immiscible with the dispersed phase. The dispersed phase 40 comprises material for producing the microparticles. The dispersed phase 40 includes dispersed material 41. The dispersed material 41 may for example, be a polymer or nanoparticles. Further, the dispersed phase may be combination thereof. Further the dispersed phase may comprise a third component such as fluorescent material, or encapsulated drug. In effect, the dispersed phase may contain any component which is desired to be included in the resulting microparticles. The dispersed phase may comprise a polymer solution or a nanoparticle suspension. The material—polymer or nanoparticles is provided to produce the microparticles. Nanoparticles in the dispersed phase may be metal oxide nanoparticles or any type of superparamagnetic nanoparticle. The nanoparticles in the dispersed phase may most preferably comprise iron or iron oxide nanoparticles. The nanoparticles may also comprise Ni or PtFe. The use of iron oxide nanoparticles, for example, $Fe_2O_3$, $Fe_3O_4$ or a mixture thereof, enables production of microparticles with a tuneable magnetisation and a high magnetic susceptibility. The magnetisation may be in the range of 20-110 emU/g. The magnetisation may be in a preferred range of 20-80 emU/G.

The phases are not premixed. Emulsification occurs upon entry of the first and second phases to the shear device. The emulsifying step occurs as the first and second phases enter the shear device. The mixing step includes an emulsifying step as the second dispersed phase is emulsified into the first continuous phase in the shear device.

The phases 30 and 40 are mixed in the shear device 10 to form the emulsion 50 comprising emulsion droplets 51.

The use of separate inlets 14 and 15 provides that the continuous phase 30 and the dispersed phase 40 flow separately into the shear device 10. Further no emulsification occurs until the phases 30 and 40 enter the device 10. This arrangement of a shear device 10 having first and second inlets 14 and 15 has been found advantageously to provide an emulsion 50 having a relatively narrow particle size distribution and for scalable production.

The shear device 10 includes a rotor 11 configured to revolve inside a stationary stator 12. A gap 13 is provided between the rotor 11 and stator 12. The gap 13 is an annular gap. Emulsification of the phases occurs in the gap 12. The shear device 10 is configured to provide control of the droplet size distribution in the emulsion 50. The shear device is controlled and the operating parameters of the shear device 10 may be varied and controlled to control the droplet size and uniformity of size distribution. The shear device is arranged to provide a uniform force therein. The droplet size is less than 50 microns. The droplet size is preferably less than 20 microns. Depending on requirements, the droplet size may be less than 10 microns.

The particle size distribution is controlled by optimising the features of the radius of the rotor 11. The particle size distribution is also controlled by optimising the gap size between the rotor 11 and stator 12. In the exemplary, arrangement described, the gap size is set at substantially 100 microns. However, it will be appreciated that a shear device having different suitable gap size depending on requirements may also be provided. The rotor is controlled to rotate inside the stationary stator. Rotation speeds of up to 2000 rpm may be applied, in general the device is operated at rates between 50 and 1000 or 50 and 1500 rpm depending on requirements. In the preferred arrangement, the rotor 11 has a radius substantially of the order of 20 cm. Referring to FIG. 3e the provision of rotor of relatively large radius $R_i$ provides for improved control of rotor rotation including speed and for increased speed of rotation.

Figure 3E:
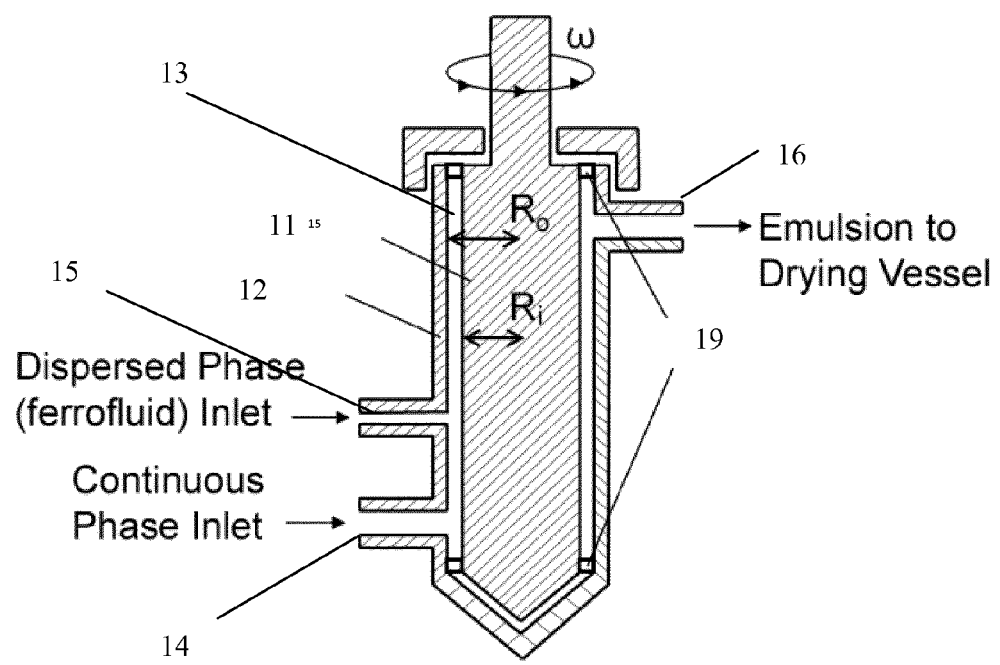

It is noted that by control of gap size and form of the rotor, there is provided a velocity distribution in the gap, see FIGS. 1B and 3D and 3E.

Viscosity of the continuous phase is important and viscosity of the continuous phase may be controlled by controlling selection of surfactant, surfactant concentration and thickening material which are selected and used at concentrations, as required.

The shear device 10 further comprises control means for controlling the rotation speed of the rotor 11 and control means for controlling the flow rate of the continuous phase 30 and the dispersed phase 40 to the shear device 10. Control of the flow rates provides control of—dispersed phase volume fraction. The arrangement of the shear device with two separate inlet ports for the different phases provides for a high level of control of the dispersed phase volume fraction.

Referring to FIGS. 3a, 3b and 3c a shear device 10 according to an arrangement of the present specification is shown. Referring to FIGS. 3d and 3e alternative shear devices 10 are shown having bearings 19 provided to maintain the gap size between the rotor 11 and stator 12 in the arrangement shown. In an exemplary arrangement of FIG. 3d a shear device 10 according to the present specification was provided having a cylindrical rotor 11 of substantially 45 mm in diameter with stainless steel ball beads 19 fitted on either end. The housing 10a comprises a cylindrical stator 12 with flanges on either end. The gap ($R_o$–$R_i$) 13 between the inner radius of the stator 12 and the outer radius of the rotor 11 is substantially 100 µm. Two circular plates 34 are bolted using bolts 30 onto either end of the stator 12, pressing against the bearings 19 to keep them tightly positioned and minimise undesired movement. The rotor 11 has a cylindrical shaft on one side which is coupled to a motor via coupling 33. One of the plates 34 has a hole in its centre through which the shaft passes. A u-ring 31 is used to prevent leakage from the device through the gap in the plate around the shaft. O-rings 32 are also provided. Couette shear mixer showing individual inlets for aqueous and dispersed phases, with emulsion outlet on top right. Droplet size was adjusted through variation of the shear rate, $\gamma'$, which for low dispersed phase volume fractions can be approximated as $\gamma'=R_i\omega/(R_o-R_i)$, where Ri is the inner rotor radius, Ro is the outer radius of the stator, and $\omega$ is the angular velocity of the rotor. Teflon O-rings were used to prevent leakage. It will be appreciated that suitable alternative spacers 19 may be provided for example o rings per the arrangement of FIG. 1.

The shear device 10 is configured to provides for scalability, and/or for large throughput and/or large scale production of microparticles, as follows:
  Separate inlet ports 14, 15 for different phases
  Emulsification occurs inside shear device 10 in gap 13
  Controllable mixing
  Controllable dispersed phase volume
  Controllable shear rate
  No emulsion premixing and no resultant phase separation of premix.
Throughput is limited only by phase syringe or reservoir capacity.

The above noted features are selected and optimised to provide for production of substantially uniform microparticles. The system and method provide for production of monodisperse particles of % CV for example, of 25% preferably substantially <25% CV. The shear device 10 has been configured to advantageously provide consistent shear rate and improved throughput. In the method 200 of particle production according to the present specification, the shear device 10 is configured to provide a minimised particle size distribution by optimisation of critical parameters.

Control of Microparticle Size and Size Distribution
  Optimisation of method and system for control of droplet/microparticle size and uniformity of size distribution include control of the following:
  Shear rate
    (selection of: rotor radius, rotor speed and gap size)
  Dispersed phase volume fraction
  Viscosity ratio between phases
Also
  Continuous phase viscosity
  Surfactant concentration
  These various parameters noted above may be optimised to allow production of microparticles having particular preferred size/properties. Some possible preferred operating parameters according to an exemplary method of the present specification include the following:
  The device is operable at shear rates of up to 2000 revolutions per minute (rpm), preferably in the range of 50-1500 rpm. In some exemplary methods according to the present application, operation has been optimised as follows: For production of spherical particles for example of 350 nm, shear rate is controlled to provide a shear rate of substantially 300 rpm (6900 per sec) or greater. For production of Crumpled/dimpled particles shear rate is controlled to provide a shear rate preferably of 50-100 rpm. For production of porous particles a shear rate in the range of 50-800 rpm is preferably used.

Dispersed phase volume fraction is controlled to provide a dispersed phase volume fraction in the range of 10-90%. For spherical particles a dispersed phase volume fraction above 50%, preferably 80% is used. For crumpled and dimpled particles a dispersed phase volume fraction of preferably 10-50%, preferably 30-50% is used.

Viscosity ratio between phases dispersed to continuous is controlled to between 0.01 and 1, most preferably 0.1.

Surfactant concentration is controlled in the range of 0.1 to 10%. The surfactant may for example comprise SDS, TX100. Tween 20. For example to produce particles of larger size a surfactant concentration to the lower end of the range may be preferred. For example, to produce particles of diameter of the order of 500 nm a concentration of 0.1% may be used.

Continuous phase viscosity is controlled by selection of thickener. Thickeners may include @ Dextran, PVP, Sucrose, (hydrophilic/non-absorbing polymer). Continuous phase viscosity is controlled by selection of surfactant. Concentration of thickener and/or surfactant is selected and controlled as required.

Control of Magnetisation of Microparticles

Figure 6:
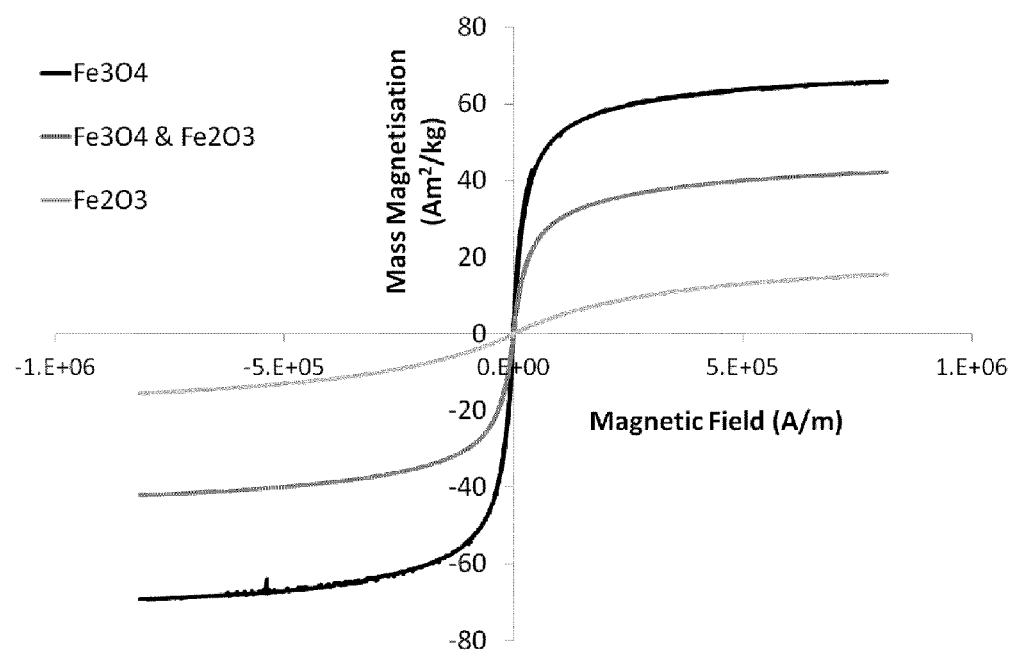
FIG. 6 is a graph showing the effect of magnetite type on magnetic moment for $Fe_3O_4$ nanoparticles, $Fe_2O_3$ nanoparticles which have a lower magnetic susceptibility and saturation magnetisation and Superparamagnetic microparticles produced using mixtures of $Fe_3O_4$ and $Fe_2O_3$ nanoparticles. The graph shows Mass Magnetization ($Am^2$/kg) vs Magnetic Field A/m.

The method further provides for control of magnetisation of microparticles, by control of type and concentration of superparamagnetic microparticles provided in the dispersed phase. As noted above the superparamagnetic particles may comprise iron oxide nanoparticles for example, $Fe_3O_4$ nanoparticles or $Fe_2O_3$ nanoparticles or a mixture thereof. $Fe_3O_4$ nanoparticles, $Fe_2O_3$ nanoparticles have lower magnetic susceptibility and saturation magnetisation and SMPs produced using mixtures of $Fe_3O_4$ and $Fe_2O_3$ nanoparticles. Referring to FIG. 6, it is noted that the use of iron oxide nanoparticles 41 enables production of microparticles 100 with a tuneable magnetisation and a high magnetic susceptibility.

Figure 5A:
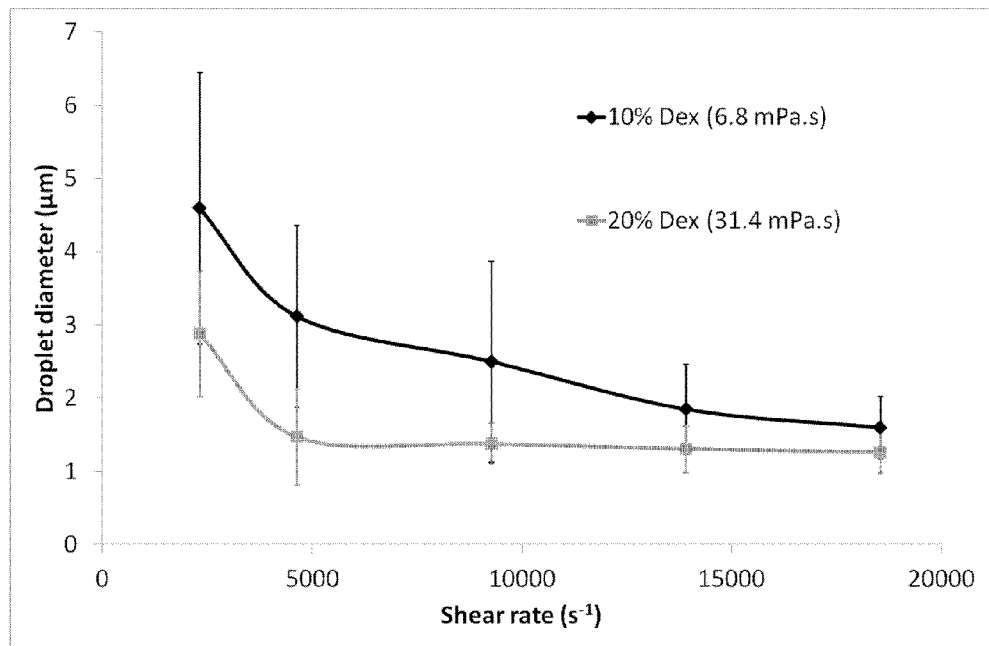
FIG. 5a is a graph showing average droplet diameter with shear rate for different continuous phase viscosity. SDS 4% (w/w), dispersed phase: Cyclohexane. Continuous phase flowrate: 0.5 mL/min, dispersed phase flowrate: 0.5 mL/min (Volume fraction of dispersed phase, φ=0.5). Error bars show standard deviation. Increasing the continuous phase viscosity results in the reduction in the average droplet size; the average droplet size with continuous phase viscosity 31.4 mPa·s is lower than those produced at 2.7 mPa·s. Droplet size variation decreases at higher rates of shear, and more uniform droplets are produced.
Figure 5B:
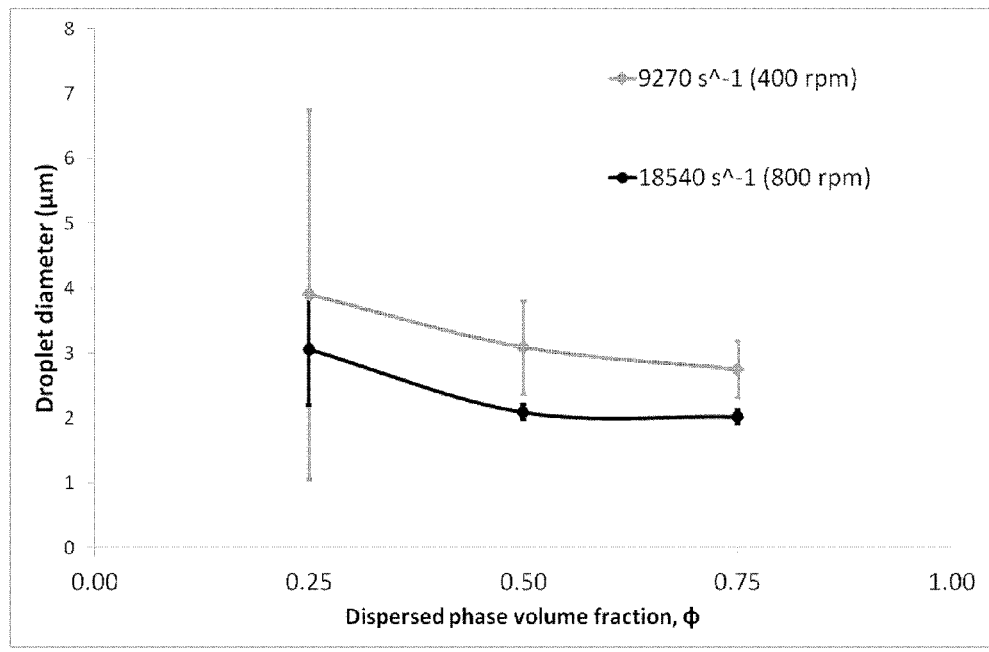
FIG. 5b is a graph showing variation in droplet diameter and uniformity as a function of dispersed phase volume fraction for different shear rates. The total flow rate of the two phases was kept constant at 1 mL/min. Continuous phase: 10% w/w Dextran, SDS 4% w/w. Dispersed phase: Cyclohexane containing dissolved nanoparticles 10 mg/mL. Microparticles with diameters greater than approximately 250 nm settled in the drying bath, and microparticles below this size remained suspended in the bath. The suspended microparticles were removed though suction and disposed of. This particle size corresponds to a droplet size of 1.87 μm for ferrofluid concentration of 10 mg/mL. Therefore, droplets below this threshold size were not included in this figure. Increasing the dispersed phase volume fraction results in a decrease in both the average droplet size and standard deviation. Droplets with narrower standard deviation were produced at shear rates of 18540 $s^{-1}$ than at 9270 $s^{-1}$.
Figure 5C:
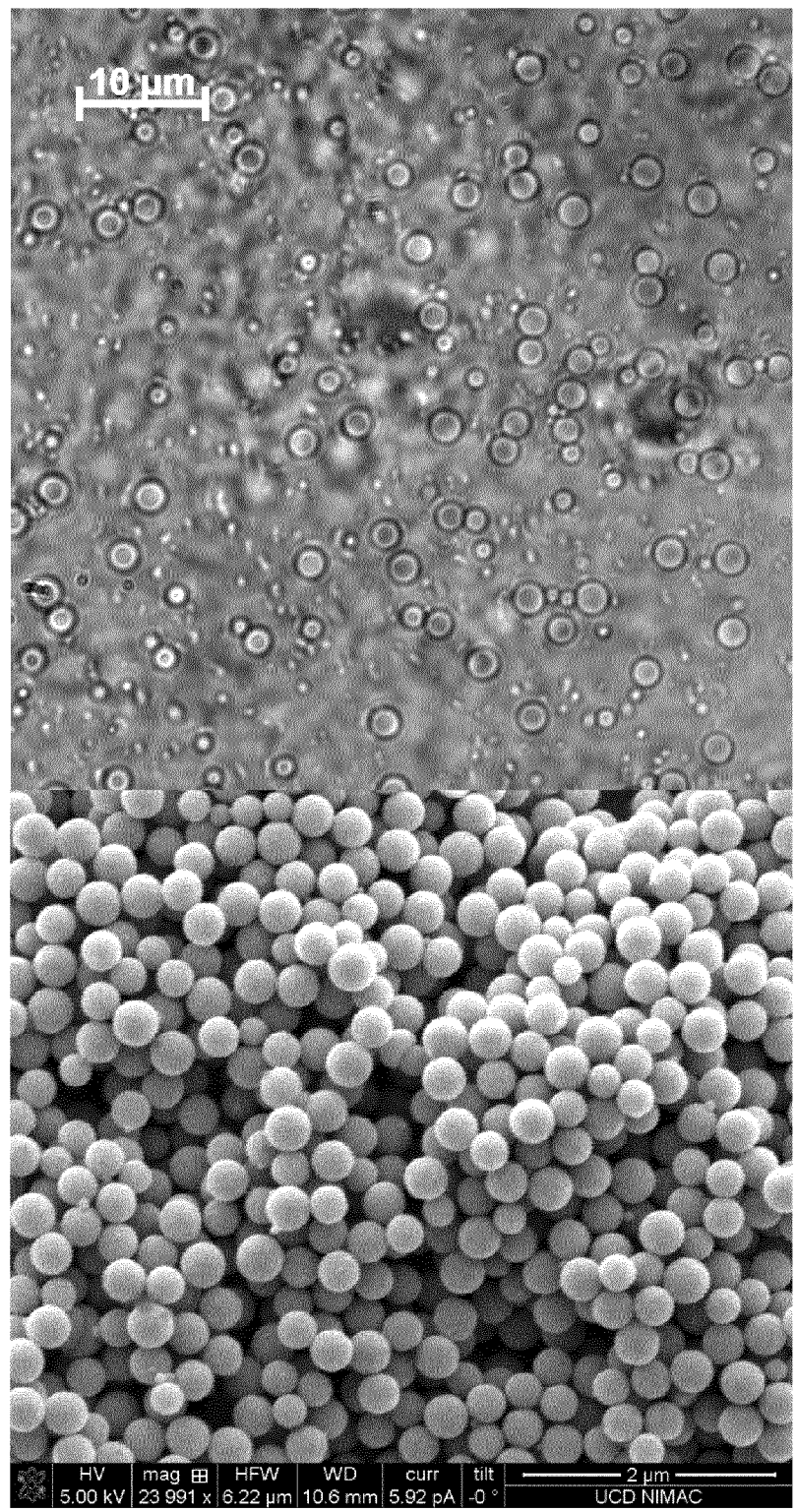
FIG. 5c: top shows light microscope image (100× mag) of emulsion droplets synthesized at shear rate 13900 $s^{-1}$ (600 rpm). Continuous phase: 10% w/w Dextran, SDS 4% w/w. Dispersed phase: Cyclohexane containing dissolved nanoparticles 10 mg/mL. Continuous phase flowrate: 0.2 mL/min. Dispersed phase flowrate 0.8 mL/min. Dispersed phase volume fraction: 0.8.

Referring to FIGS. 4 and 5a and 5b the effects of varying shear rate and different disperse phase volume fractions are illustrated in graphical form. Referring to FIG. 5c images of droplets synthesized at shear rate 13900 $s^{-1}$ (600 rpm) are shown.

In the arrangement of the system 1, the shear device 10 is further connected to the drying device 20 for having control means for drying the emulsion droplets 51, as required. The drying device is a drying bath 20 having control means for controlling drying including for example the drying rate.

Control of Microparticle Morphology

Microparticles 100 of a particular required morphology are formed by controlling parameters including:
nanoparticle concentration
surface chemistry, and
rate of drying
ratio of dispersed phase The system and method of the present specification provide that microparticles 100 of different morphologies for example, spherical, crumpled, dimpled or porous or hollow may be formed as required by suitable control of one or more of the above parameters.

Nanoparticle concentration is controlled preferably in the range of 0.1 to 200 mg/ml is used. Concentrations of 0.1-0.5 mg/ml may be preferably used for the production of crumpled or dimpled microparticles. Concentrations of 80 mg/ml may preferably be used for the production of hollow/porous microparticles.

Surface Chemistry.

In a method according to the present specification, the surface chemistry of oleic acid ligands on the surface of the nanoparticles is controllable to produce microparticles of crumpled morphology. Discussed further below with reference to FIG. 12 and examples.

Rate of Drying.

The rate of drying is controllable to control the formation of microparticles of different morphology.

Referring to FIG. 1, the drying bath 20 is an enclosed drying bath. The drying bath 20 includes heating means 22 and an agitation means, the agitation means is for example an impellor 23 for mixing the emulsion 50 in the drying bath. The drying bath 20 has control means 21 for controlling the temperature. In the case of the drying bath 20 it is possible to vary the temperature substantially between 5 and 80 degrees Celsius. As the drying bath is enclosed it is possible to control the dispersed phase vapour pressure during drying. The impellor 23 is controlled to control mixing to vary the impellor mixing speed. The impellor is operable up to a mixing speed of 400 RPM.

Referring to FIG. 7 a figurative illustration of a method of drying is provided. FIG. 8 shows images of particles of different morphologies formed according to a method of the present specification.

An exemplary arrangement and method according to the present specification is described with reference to FIGS. 1 and 2. The continuous phase 10 is an aqueous phase. The continuous phase 10 further includes a surfactant 11, for example SDS, TX-100, Tween 20 and a thickener 12, for example Dextran, PVP, Sucrose (hydrophilic/non-absorbing polymer). The dispersed phase 20 comprises a nanoparticle suspension. The nanoparticles 41 are particles having dimensions of the order of 10 nm. The nanoparticles 41 of an exemplary arrangement of the present specification as described comprise iron oxide or $Fe_3O_4$ or $Fe_2O_3$ nanoparticles. The dispersed phase 40 comprises nanoparticles 41 of $Fe_3O_4$ dissolved in an organic solvent 42. FIG. 6 is a graph illustrating the effect of magnetite type on magnetic moment for $Fe_3O_4$ nanoparticles, $Fe_2O_3$ nanoparticles have lower magnetic susceptibility and saturation magnetisation and SMPs produced using mixtures of $Fe_3O_4$ and $Fe_2O_3$ nanoparticles. Referring to FIG. 6, it is noted that the use of iron oxide nanoparticles 41 enables production of microparticles 100 with a tuneable magnetisation and a high magnetic susceptibility. The organic solvent 42 may be for example, Hexane, Cyclohexane, Toluene, Pentane, dichloromethane, pentene. The concentration of nanoparticles 41 in the dispersed phase 40 is substantially in the range of 0.1-200 mg/mL. It will be appreciated that while in the example described nanoparticles 41 comprising iron oxide nanoparticles, suitable alternative superparamagnetic particles may also be used. Further it will be appreciated that the system and the method of the present specification may be used with suitable alternative dispersed material provided in the dispersed phase for example a polymer to produce polymeric microspheres.

The concentration of nanoparticles 41 in the dispersed phase 40 may be controlled and varied as required to provide microparticles 100 of different morphologies. The concentration of nanoparticles 41 in the dispersed phase 40 is decreased (relative to that used to provide spherical microparticles) to provide microparticles 100 of dimpled morphology and further decreased to provide microparticles 100 of crumpled morphology.

Referring to FIG. 9, varying the concentration of iron oxide nanoparticles 41 in the dispersed phase 40 between 0.1 and 1 mg/ml is shown to affect microparticle morphology. At a nanoparticle concentration substantially at or above 1 mg/ml the microparticles 100 are smooth and spherical. At a nanoparticle concentration of 0.5 mg/ml, the microparticles 100 are dimpled. At a nanoparticle concentration of 0.1 mg/ml, the microparticles 100 have a crumpled morphology. The dispersed phase may comprise nanoparticles having a particle diameter of between 3 and 30 nm, most preferably 5 and 15 nm.

The continuous phase 30 and the dispersed phase 40 are provided to the inlets 14 and 15 respectively from individual continuous phase and dispersed phase reservoirs 17 and 18. There is no premixing of the phases 30 and 40. Emulsification takes place in the shear device 10 directly. The production run time is advantageously limited only by the capacity of the reservoirs. No premixing of phases is required and there are no issues of separation of premixed phase affecting the duration of a production run for producing microparticles.

Method

The method 200 of production of microparticles 100 according to the present specification is an emulsion based/templated synthesis route. The emulsion based synthesis route described is an oil in water emulsion based synthesis route. However, it will be appreciated that a water in oil emulsion based synthesis route could also be used.

Referring to the drawings and in particular FIG. 2 a method 200 of the present specification for producing microparticles 100 is described. The method 200 includes in a preparing step 201 preparing the first continuous phase 30 and the second dispersed phase 40 to the required specifications. The method further includes a first mixing or emulsifying step 210 and a second drying step 220. According to the method 200, continuous phase 30 and dispersed phase 40 are provided via separate inlets 14 and 15 to the shear device 10. In the emulsifying step 210 the continuous and dispersed phases are mixed to produce emulsion 50 of emulsion droplets 51. The control of the mixing and emulsifying step 210 controls the size and size distribution of emulsion droplets 51. Control of the mixing and emulsifying step 210 includes control of operation of the shear device including shear rate, flow rates of the continuous and dispersed phases into the device. The drying step 220 controls the morphology of microparticle 100. Control of the morphology is also provided by the selection of components of the continuous and dispersed phases. Other parameters of the method which may also be varied to control size and morphology of microparticles have been discussed above. In practice, a number of different parameters of the method are controlled and varied to control size and morphology of the microparticles, as required.

Emulsifying Step

By controlling and varying parameters of the mixing or emulsifying step 210 it is possible to control the emulsion droplet size and size distribution.

The flow rates of the continuous phase 30 and dispersed phase 40 to the shear device 10 are controlled as required. The continuous phase 10 is provided to the shear device 2 in a preferred exemplary arrangement at a flow rate of up to 4 mL/minute. The dispersed phase 20 is provided to the shear device 2 in a preferred exemplary arrangement at a flow rate of up to 2 mL/minute. The dispersed phase 40 volume fraction is controlled during the emulsifying step 210 by the use of the separate ports 14 and 15 for the continuous and dispersed phases 30 and 40. Control of the flow rate of the two phases 30 and 40 provides for control of the viscosity ratio between the phases. Importantly, the provision of two separate inlet ports as described allows for the dispersed phase to be provided into the continuous phase in the shear device.

Other parameters which may be varied in the emulsifying step 210 include the shear rates of the continuous phase 30 and the dispersed phase 40. Further the diffusion rate of the continuous and the dispersed phases 30, 40 may be controlled to tune the microparticle 100 morphology. Further the diffusion rate of the dispersed phase solvent in the continuous phase 30, 40 may be controlled to tune the microparticle 100 morphology.

The emulsification step 210 controls the droplet (and therefore microparticle 100) size and size distribution, and the drying step 220 determines the microparticle morphology.

The factors affecting the step 220 of drying the droplet 51 and associated particle aggregation include, the following:
Nanoparticle concentration in the dispersed phase
Nanoparticle surface chemistry
Temperature of drying bath
Degree of mixing of drying bath through impellor
Solubility of dispersed phase solvent in continuous phase
Drying bath head space vapour pressure
Dispersed phase volatility One or more of the above parameters may be adjusted or varied, as required.

Drying Step

By controlling and varying parameters of the drying step 220 it is possible to control morphology of the microparticles 100. In particular by controlling the drying of the emulsion 50 it is possible to control the morphology and therefore the surface area and volume ratios of the microparticles 100. In the drying step 220, it is possible to control the mixing speed by controlling and varying the speed of operation of the impellor 23. The mixing speed is varied up to 400 RPM. The temperature is controlled as required. The temperature is varied between 5 and 80 degrees Celsius as required. The dispersed phase vapour pressure is controlled and varied as required.

Some of the parameters of the method 200 e.g. nanoparticle concentration in dispersed phase are set prior to the emulsion droplets 51 entering the drying bath 20. However parameters such as temperature, degree of mixing, and head space vapour pressure are properties of the drying bath 20, and are controllable in the drying step 220 to achieve the desired drying rate and microparticle 100 morphology. Therefore, the use of an enclosed drying bath 20 with precise control over these parameters is required subsequent to the emulsification step 210.

Referring to FIG. 7, there is provided an illustration of drying to form microparticles of different morphology.

The drying step 220 according to the method of the present specification provides greater control of microparticle 100 morphology than for example prior spray drying techniques. Microparticles 100 are provided according to the present specification. The system 1 and method 200 provide for the production of microparticles 100 with a high level of control of the microparticle morphology and properties. Microparticles 100 of a production run of method 200 have high levels of uniformity of microparticle size and morphology. Other properties of microparticles 100 include particles have a high surface area per unit volume. Microparticles 100 having different morphologies have been produced including crumpled and dimpled microparticles and porous microparticles 100.

Microparticles 100 may comprise superparamagnetic microparticles. Superparamagnetic microparticles 100 have a high magnetic separation velocity. Microparticles 100 may be polymer coated if required.

Referring to FIGS. 9A-C SEM images of superparamagnetic microparticles 100 produced with ferrofluid nanoparticle concentrations of 1 mg/ml, 0.5 mg/ml and 0.1 mg/ml respectively are shown showing the transition from spherical to dimpled and crumpled particles with decreasing nanoparticle concentration. Referring to FIGS. 9 D-F TEM images of cross-sections of spherical, dimpled and crumpled microparticles. The hollow area inside the dimpled and crumpled microparticles 100 indicate that a nanoparticle shell developed at the surface of the emulsion droplet during drying which then collapsed inward as drying continued.

The hollow nature of the dimpled and crumpled particles indicates that the particles were formed through a shell formation and buckling mechanism.

Figure 10:
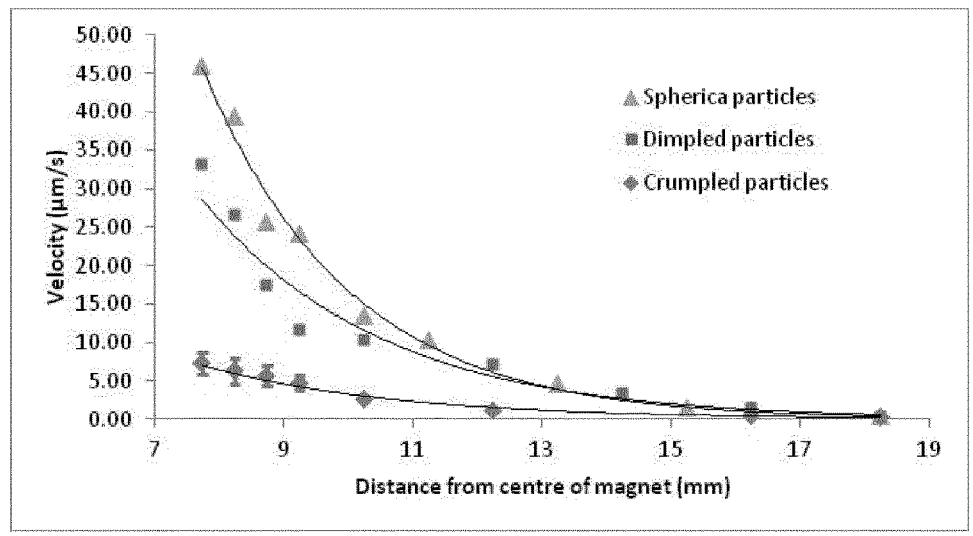
FIG. 10 is a graph showing the velocity of the different morphology microparticles of diameter 1.2±0.2 μm (largest cross sectional diameter measured for dimpled and crumpled microparticles) with distance from a fixed magnetic field.
Figure 11:
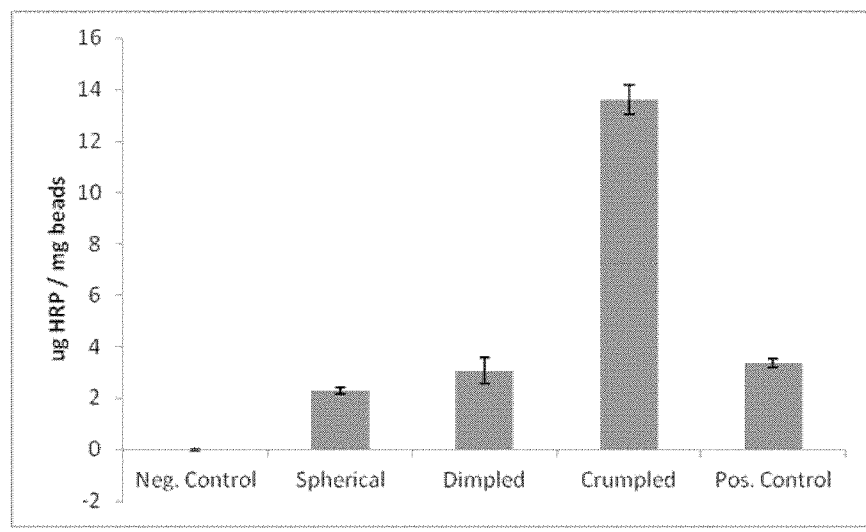
FIG. 11 is a graph showing binding capacity of avidin functionalised beads of different morphology expressed in μg Biotin-HRP per mg of beads. Streptavidin Dynal M-270 beads were used for the positive control, with carboxyl functionalised spherical in-house beads used for the negative control. Non-specific binding was blocked by incubation with BSA 0.2% w/w prior to conjugation of Biotin-HRP to the beads.

Referring to FIG. 10 crumpled microparticles 100 are shown to have a magnetic separation velocity substantially six times lower than spherical particles (SMPs) of equivalent diameter. Dimpled particles were shown to have a velocity substantially 1.3 times lower than spherical SMPs. Further the crumpled microparticles were found to have a surface area per unit volume substantially seven times higher than that of spherical particles of similar diameter. Referring to FIG. 11 it is shown that crumpled microparticles 100 have a binding capacity per unit volume substantially seven times higher than for example spherical particles of equivalent diameter.

For comparison, to assist in highlighting the properties of the crumpled particles of the present specification, it is noted that if one were to use a spherical particle with a diameter selected to offer the same surface area to volume ratio as a crumpled particle 1 μm in diameter, it would have a diameter of 0.15 μm and a separation velocity 60 times lower than that crumpled particle, and 300 times lower than a spherical particle 1 μm in diameter. It has for example been demonstrated that Dynal M-270 beads have a volume magnetisation approximately 6 times lower than the Spherical particles (SMPs). Assuming the volume magnetisation of the Dynal 1 μm beads and Dynal M-270 beads to be the same, it can be concluded that Dynal 1 μm beads have a magnetic separation velocity 6 times lower than internally produced spherical particles 1 μm in diameter. The magnetic separation velocity of the 1 μm crumpled particles according to the present specification is equivalent to the separation velocity of spherical 1 μm Dynal beads from Invitrogen, while the surface area per unit volume is substantially 6-7 times higher.

Figure 12:
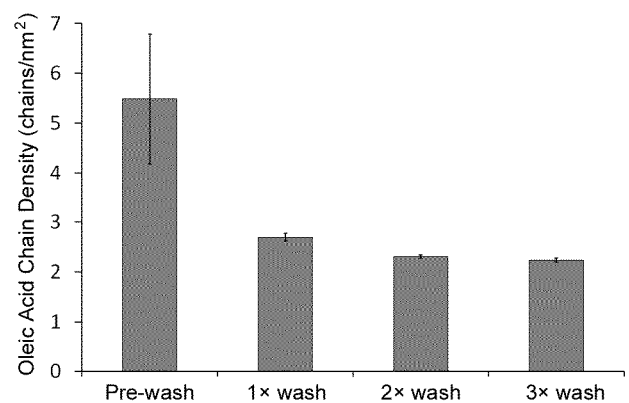
FIG. 12 is a graph of Oleic acid chain density on iron oxide nanoparticles before and after washing steps with ethanol. Removal of oleic acid side chains on nanoparticles decreases their hydrophobicity and therefore increases their affinity for the oil-water interface.
Figure 13:
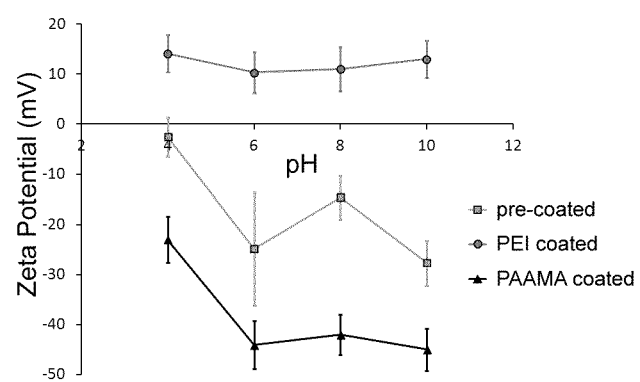
FIG. 13 is a graph of Zeta-potential values of spherical SMPs at different steps during the polymer coating procedure, from uncoated particles (squares) to amine- (circles) and carboxyl-functionalized (triangles) microparticles. The change in the value of zeta-potential indicates that each coating step successfully modified SMP surfaces. Error bars show standard deviation.

Referring to FIG. 12 In an exemplary arrangement the formation of a shell during droplet drying may be explained by an increased affinity of the iron oxide nanoparticles for the oil-water interface. Oleic acid chains bound to the nanoparticles make them oil-soluble and also act as a stabilizer to prevent undesired aggregation. Incomplete coverage of the nanoparticles with oleic acid may result in a reduction of their hydrophobicity and, correspondingly, an increased affinity for the oil-water interface, leading to their accumulation and locking at the surface of the droplet. In order to investigate this hypothesis, the density of oleic acid side chains on the iron oxide nanoparticles was measured for the stock ferrofluid (the resulting microparticles are shown in FIG. 9) and after washing with ethanol. The oleic acid chain density on the nanoparticles in the stock ferrofluid, and after a number of ethanol washes, is shown in FIG. 12. A close-packed monolayer of oleic acid on a flat surface corresponds to ~4.17 chains/nm The stock nanoparticles (5.48 chains/nm2) therefore have a monolayer of adsorbed oleic acid, with the density higher than the close-packed value attributable to the curvature of the nanoparticles. The chain density is depleted to 2.31 chains/nm2 after two ethanol washing steps, which corresponds to a submonolayer coverage of ~42% on the nanoparticles. Hence, the contact angle of the nanoparticles changes after washing so that they have a greater affinity for the oil-water interface and also a greater tendency to aggregate with each other. After a third ethanol wash, nanoparticles could no longer be fully redissolved in hexane due to the decrease in their hydrophobicity. In order to assess the effect of oleic acid density on microparticle morphology, SMPs were synthesized with nanoparticles that were washed twice with ethanol. According to an exemplary methods micro-particles produced with 1 g/L ethanol-washed nanoparticles are mostly crumpled (FIG. 14A). SMPs produced using the unwashed nanoparticles with a mono layer of oleic acid and at the same nanoparticle concentration (1 g/L) are spherical (FIG. 9A). Therefore, when the nanoparticle concentration is kept constant, the nanoparticle chain density influences the drying route to that of either spherical or crumpled microparticles. This indicates that the nanoparticle chain density determines their affinity for the interface and aggregation to each other and thus the likelihood of the formation of a shell of nanoparticles at the interface. To investigate if the nanoparticle concentration influences the resulting microparticles, SMPs were synthesized with 5 g/L ethanol-washed nanoparticles (i.e., submonolayer oleic acid coverage). The SMPs were found to be dimpled (FIG. 14B), suggesting that nanoparticle concentration, independently of nanoparticle oleic acid coverage, influences the drying route and resulting microparticle morphology. From these results it can be inferred that the microparticle morphology depends on two factors: (i) the density of oleic acid chains attached to the nanoparticles and (ii) the concentration of iron oxide nanoparticles in the ferrofluid. The oleic acid chain density on the nanoparticles affects the rate of nanoparticle aggregation events and therefore the number of seed nuclei. The nuclei are drawn to the energy well at the oil-water interface due to amphiphilic nature of the oleic acid-deficient nanoparticles. The concentration of nanoparticles then may determine the growth rate of the seed nuclei and, by mass balance, the thickness of the shell of densely packed nanoparticles that forms at the droplet interface. The thickness of the formed nanoparticle shell in turn affects its structural stability, as the critical buckling stress of a thin elastic spherical shell is proportional to the square of the thickness, $Pc=2Et2/(r2(3(1-v2))^{1/2})$, where E is the Young's modulus, r is the shell radius, v is the Poisson ratio, and t is the shell thickness. The thicker shells that form at higher nanoparticle concentrations are stronger and more resistant to buckling, and therefore likely to collapse inward at only one location, unlike the thinner shells that form at low nanoparticle concentrations and buckle at multiple locations as drying proceeds. In this way, dimpled and crumpled microparticles form at higher and lower nanoparticle concentrations, respectively. In addition, buckling of the shell may also be hindered due to spatial constraints within the droplet at higher nanoparticle concentrations. In the case of the microparticles shown in FIG. 9B, C, diluting the stock to the desired nanoparticle concentration with hexane also decreases the free oleic acid concentration, which in turn resulted in the detachment of oleic acid from the nanoparticles to maintain the equilibrium between bound and free oleic acid moieties (the solubility of oleic acid in hexane is assumed to be similar to that of stearic acid, i.e., ~16 g/L38). Hence, the density of oleic acid chains on the nanoparticle surface decreases when the stock ferrofluid is diluted. Diluting the stock therefore had the combined effect of reducing both the nanoparticle oleic acid density and the nanoparticle concentration in the dispersed phase, both of which lead to shell formation and subsequent buckling during drying to form dimpled and crumpled SMPs.

Microparticles formed by a method and system according to the present specification are typically in the size range to 100 nm to 20 microns.

Exemplary methods describing production of microparticles 100 according to the present specification and the method 200 are described as follows. The exemplary methods are intended to assist in the understanding of the invention and are not intended to be limiting. Example 1 relates to the general synthesis route up to the point where the bare unfunctionalized particles, Examples 2-9 relate to synthesis of microparticles of the different morphologies described, and Examples 10-11 cover the particle functionalisation and their applications. Example 12 relates to magnetic mobility measurement.

Example 1

Hydrophobic Nanoparticles (Ferrofluid) Synthesis 48 g $FeCl_2 \cdot 4H_2O$ and 98 g $FeCl_3 \cdot 6H_2O$ were dissolved in 250 ml deoxygenated water in a 1 L three neck under $N_2$ atmosphere. The flask was placed into an ice bath whilst ammonium hydroxide 200 ml added rapidly with vigorous stirring. The solution was kept at 0° C. for 45 min, after which the solution was heated to 85° C. for 1 h, before 30 ml of Oleic acid was added and continued to heat for a further 60 mins. The flask was allowed to cool to room temperature before being transferred to a 600 ml beaker. A magnet was placed next to the beaker to collect the black precipitate, which was washed three times with ethanol 200 ml, after each wash a magnet was placed next to the beaker and the ethanol solution poured to waste. This process was repeated with DI water 200 ml three times followed by 20% perchloric acid 200 ml three times, DI water 200 ml three times and finally ethanol 200 ml three times. After the last ethanol wash the solution was poured away and hexanes 400 ml was added to the beaker. The black precipitate (iron oxide nanoparticles) was easily dispersed in hexane resulting in a nonaqueous ferrofluid.

When additional washing steps were required, stock ferrofluid (5 mL, 90 mg/mL) may be mixed with ethanol (35 mL) in a 50 mL centrifuge tube. The nanoparticles were dispersed in the mixture by sonication and vigorous mixing. The mixture was then centrifuged at 4000 rpm in a Rotina 420R centrifuge (Hettich, Tuttlingen, Germany). The supernatant was decanted, and a fraction of the sediment (ca. 100 mg) was removed and dissolved in hexane—this ferrofluid was washed once. The remainder of the sediment was resuspended in ethanol (40 mL) and centrifuged as before. This procedure was repeated 3×, after which the iron oxide nanoparticles could not be fully redissolved in hexane.

Emulsification Using Couette Mixer

A continuous phase consisting of a thickener such as Dextran (Mw 50-650 kDa) 5-30% w/w or Polyvinylpyrrolidone (1300 kDa) 5-30%, and containing a surfactant such as SDS, Triton X-100 or Tween 20 at 0.1-20% w/w 50 mL, and hexane 50 mL containing dissolved iron oxide nanoparticles at concentrations between 0.1 and 200 mg/mL were pumped into the couette mixer at different inlet ports. The aqueous phase was pumped at a rate of 0.2-4 mL/min and the organic phase at a rate of 0.2 to 4 mL/min. The droplet size was adjusted through variation of the shear rate and the dispersed phase volume fraction (See FIGS. 5A and 5B). The homogenised emulsion was collected in a drying bath (500-5000 mL containing a surfactant such as SDS, Triton X-100, Tween etc.) under gentle agitation (150-170 rpm) and the emulsion was left to dry for 24 hours. The collected microparticles were washed with 0.5% Triton-100 solution for 2 times to remove residual dextran.

Emulsion/SMP Size Characterization

Images of the emulsion droplets were obtained using a Zeiss microscope with a 60× or 100× objective lens in Differential Imaging Contrast (DIC) mode. SEM Images of the microparticles were obtained using a Hitachi TM-1000 or FEI Quanta 30 FEG Dualbeam. Optical sizing software (Axiovison 4.8) was used to measure droplet and microparticle size distributions from the obtained images. More than 80 data points were used when measuring size distributions of superparamagnetic particles and emulsion droplets.

Magnetic Properties Measurement

Magnetic properties were performed on a Quantum Design Magnetic properties measurement system, MPMS, Superconducting Quantum Interference Device. Iron content was analysed using atomic adsorption.

Example 2—Synthesis of Spherical Microparticles with Narrow Size Distribution (CV<25%) (ϕ300 to 500 nm) (See FIG. 5c)

Dextran (50-150 kDa) 10% w/w, SDS 4% w/w solution 20 mL and hexane 80 mL containing dissolved iron oxide nanoparticles at concentration 10 mg/mL were pumped into the couette mixer through separate inlet ports. The aqueous phase was pumped at a rate of 0.2 mL/min feeding speed and the organic phase at a rate of 0.8 mL/min. The rotor speed was adjusted to 600 rpm (13900 $s^{-1}$). The homogenised emulsion was collected in a drying bath (850 mL at 0.5% Triton) under gentle agitation (150-170 rpm) and the emulsion was left to dry for 24 hours. The microparticles that had settled after 24 hours were collected and washed with 0.5% Triton-100 solution for 2 times to remove residual dextran.

Example 3—Synthesis of Spherical Microparticles with Narrow Size Distribution (CV<25%) (ϕ70-250 nm)

Polyvinylpyrrolidone (1300 kDa) 15% w/w, SDS 4% w/w solution 20 mL and hexane 80 mL containing dissolved iron oxide nanoparticles at concentration 10 mg/mL were pumped into the couette mixer through separate inlet ports. The aqueous phase was pumped at a rate of 0.2 mL/min feeding speed and the organic phase at a rate of 0.8 mL/min. The rotor speed was adjusted to 300 rpm (6950 $s^{-1}$) The homogenised emulsion was collected in a drying bath (850 mL at 0.5% Triton) under gentle agitation (150-170 rpm) and the emulsion was left to dry for 24 hours. Using a magnet the microparticles were collected on the bottom for 2 h and washed with 0.5% Triton-100 solution for 2 times to remove residual dextran.

Example 4—Synthesis of Spherical Microparticles with Narrow Size Distribution (CV<25%) (ϕ500-10000 nm)

Dextran (50-150 kDa) 5-10% w/w, SDS 0.5-4% w/w solution 50 mL and hexane 50 mL containing dissolved iron oxide nanoparticles at concentration 10-50 mg/mL were pumped into the couette mixer through separate inlet ports.

The aqueous phase was pumped at a rate of 0.2-0.8 mL/min feeding speed and the organic phase at a rate of 0.2-0.8 mL/min. The rotor speed was adjusted to 100-800 rpm (2320-18540 s$^{-1}$) The homogenised emulsion was collected in a drying bath (850 mL at 0.5% Triton) under gentle agitation (150-170 rpm) and the emulsion was left to dry for 24 hours. The microparticles that had settled after 24 hours were collected and washed with 0.5% Triton-100 solution for 2 times to remove residual dextran.

The microparticles were then carboxyl coated according to the procedure outlined in Example 7. For isolation of the largest size fractions, 0.5 mg/mL microparticle suspensions (500 mL) were centrifuged at 100-4000 rpm for 3 min, the speed dependant on the size of the microparticles to be isolated. The sediment microparticles were resuspended in DI water and sonicated for 1 min, and the process was then repeated until the desired size and uniformity of the microparticles was achieved.

Example 5—Synthesis of Crumpled/Dimpled Microparticles

Dextran (50-150 kDa) 25% w/w, SDS 2-4% w/w solution 30 mL and hexane 10 mL containing dissolved iron oxide nanoparticles at concentration 0.5 mg/mL were pumped into the couette mixer through separate inlet ports. The aqueous phase was pumped at a rate of 0.75 mL/min feeding speed and the organic phase at a rate of 0.25 mL/min. The rotor speed was adjusted to 50-300 rpm (1160-6950 s$^{-1}$) The homogenised emulsion was collected in a drying bath (850 mL at 0.5% Triton) under gentle agitation (150-170 rpm) and the emulsion was left to dry for 24 hours. The microparticles that had settled after 24 hours were collected and washed with 0.5% Triton-100 solution for 2 times to remove residual dextran.

There are Further Provided Exemplary Methods According to the Present Specification for the Production of Porous and Hollow Microparticles as Follows

Example 6—Porous Microparticle Synthesis (FIG. 1) Referring to FIG. 1 a 25% w/w dextran 30 mL (Mw 75 kDa) was pumped into the couette mixer at a rate of 0.75 mL/min, and hexane 10 mL containing hydrophobized iron oxide nanoparticles 15 mg/ml and 5% w/w oleic acid (Fisher Scientific) was pumped into the mixer at a rate of 0.25 mL/min. The rotor speed was adjusted to between 100 to 200 RPM.

The emulsion was transferred to an evaporation dish containing 800 ml water at 0.5% w/w Triton X-100 (Sigma Aldrich) under gentle agitation. After 24 hours the dried microspheres 500 were collected with a magnet and washed with 0.5% Triton X-100 solution to remove residual dextran.

Example 7—Porous Microparticles Synthesis Alternative (FIG. 1) Referring to FIG. 1 a 10% w/w dextran 30 mL (Mw 75 kDa) containing 2% w/w SDS was pumped into the couette mixer at a rate of between 0.75 to 0.9 mL/min, and hexane 10 mL containing hydrophobized iron oxide nanoparticles 80 mg/mL was pumped into the mixer at a rate of between 0.25 to 0.1 mL/min. The total flowrate of the dispersed and continuous phases was 1 mL/min. The rotor speed was adjusted to between 100 to 200 RPM.

The emulsion was transferred to an evaporation dish and allowed to dry under no agitation. After 24 hours the dried microspheres 500 were collected with a magnet and washed with 0.5% Triton X-100 solution to remove residual dextran.

Example 8—Porous Microparticles Synthesis Alternative 2

(FIG. 1) Referring to FIG. 1 a 10% w/w dextran 30 mL (Mw 75 kDa) containing between 0.1 and 0.5% w/w SDS was pumped into the couette mixer at a rate of between 1 and 3 mL/min, and hexane 10 mL containing hydrophobized iron oxide nanoparticles 15 mg/mL was pumped into the mixer at a rate of between 0.25 to 1 mL/min. The rotor speed was adjusted to between 100 to 200 RPM.

The emulsion was transferred to an evaporation dish containing 800 ml water at 0.5% w/w Triton X-100 (Sigma Aldrich) under gentle agitation. After 24 hours the dried microspheres 500 were collected with a magnet and washed with 0.5% Triton X-100 solution to remove residual dextran.

Example 9—Hollow Microparticles Synthesis (FIG. 1) Referring to FIG. 1 a 10% w/w dextran 30 mL (Mw 75 kDa) containing between 0.1 and 0.5% w/w SDS was pumped into the couette mixer at a rate of between 0.75 and 3 mL/min, and hexane 10 mL containing hydrophobized iron oxide nanoparticles 80 mg/mL was pumped into the mixer at a rate of between 0.25 to 1 mL/min. The rotor speed was adjusted to between 100 to 200 RPM.

The emulsion was transferred to an evaporation dish containing 800 ml water at 0.5% w/w Triton X-100 under gentle agitation. After 24 hours the dried microspheres 500 were collected with a magnet and washed with 0.5% Triton X-100 solution to remove residual dextran.

Some exemplary applications of the use of microparticles are described as follows:

Microparticles may be functionalised as required for different applications. In an exemplary method described to assist in understanding the present method and properties of microparticles produced by the method. The examples are not intended as limiting.

Example 10—Polymer Coating and Avidin Functionalisation of Microparticles and Binding Capacity of Biotin-HRP Measurement Dried microparticles were resuspended in a solution of 0.05% (w/w) Triton X-100, 250 mM NaCl, and 4.5% (w/w) PEI (50 mL total). The microparticle suspension was gently mixed, sonicated for 2 min and incubated at RT for 16 h. The microparticles were washed 3× with 250 mM NaCl 25 mL with 30 s sonication steps between each wash. The microparticles were then resuspended in a solution composed of 250 mM NaCl and 5% (w/w) PAAMA (50 mL total; pH=4.0). The suspension was mixed, sonicated for 2 min, and incubated at RT for 6 h. The microparticles were washed 3× with 250 mM NaCl (25 mL), resuspended in MES buffer 40 mL (pH=6.3), and sonicated for 2 min. EDC (10 mg) in MES buffer (1 mL) (pH=6.3) was added to the microparticles, and the suspension was mixed and incubated for 30 min. The carboxylated microparticles were then washed 3× with and resuspended in DI water. Carboxylated microparticles 1 mg were suspended in 1 mL MES buffer (pH=6.3) containing EDC (10 mg) and Sulfo-NHS (10 mg) and incubated at RT for 30 min. Microparticles were washed and incubated in MES buffer 1 mL (pH=6.3) containing avidin (1 mg) at RT for 2 h on a rotating wheel. Avidin-functionalized microparticles were washed and incubated in PBS buffer (1 mL) containing 0.1% (w/w) Tween 20 and 0.2% (w/w) BSA (pH=7.4) at RT for 30 min. Microparticles were then washed and incubated in PBS (1 mL) containing 0.1% (w/w) Tween 20 and Biotin-HRP 200 μg (pH=7.4) at RT for 30 min on a rotation wheel. Microparticles were thoroughly washed and resuspended in PBS (500 μL) containing 0.1% (w/w) Tween 20 (pH=7.4). 5, 10, or 20 μL of this solution was diluted with PBS (200 μL) containing 0.1% (w/w) Tween 20 (pH 7.4), followed by the addition of 150 μL of ABTS indicator solution. The reaction was stopped after 3 min by adding 0.02% (w/w) sodium azide (50 μL), and the absorbance at 410 nm was measured using a Nanodrop 2000c spectrophotometer (Thermo Scientific, Dublin, Ireland).

Example 11—Silica Coating of Microparticles and DNA Extraction

Microparticles 1 mg were suspended in a solution of Ethanol 1 mL, De-Ionized water 100 μL, Tetraethylorthosilicate (TEOS) 50 μL and mixed on rotating wheel at RT for 15 mins. Ammonium hydroxide ($NH_3OH$) 20 μL was added and the solution was mixed on the rotating wheel at RT for 6 hours. The microparticles were sonicated at 1 hour intervals. The silica coated microparticles were collected with a magnet and washed 3 times with De-Ionized water.

Silica coated microparticles 1 mg was suspended in Guanidine Hydrochloride 1 ml containing Salmon Sperm DNA 400 μg/mL. The suspension was incubated on a rotating wheel at RT for 10 hours. The microparticles were removed using a magnet, the concentration of DNA remaining was measured using a UV-Vis spectrophotometer, and the change in the DNA concentration from the start to the end was calculated.

Example 12—Microparticle Magnetic Mobility Measurement

The magnetic mobility of microparticles was measured by applying magnetic forces on particles immersed in a viscous fluid, as reported in our previous work. A magnetic field was imposed by two pairs of NdFeB magnets (12.7×12.7×6.35 mm per pair; Apex Magnets, Petersburg, W. Va.) with the same poles facing each other over a 1 mm air gap. An aluminum magnet holder attached to a micromanipulator (Eppendorf, Hamburg, Germany) was used to position the magnets at specified distances from the imaging field of an inverted microscope (Zeiss). 20 μL of magnetic microparticle suspension, containing ca. 50 000 particles in 55% (w/w) sucrose solution (viscosity=28 mPa·s), was added to a polystyrene microwell (Nunc, Rochester, N.Y.) and covered with a glass coverslip (Menzel, Braunschweig, Germany) to minimize evaporation. Fluoresbrite Plan YG 1 μm fluorescent particles (Polysciences Inc., Eppelheim, Germany) were also present in the well as positional references. The force acting on a SMP in high magnetic field gradient is calculated as $F=mM_s\nabla H$, where m is the mass of the microparticle, $M_s$ is the saturation mass magnetization of the microparticle, and H is the external magnetic field. The acting force is equal and opposite to the drag force, which is calculated using the Stokes-Einstein relation: $F=6\pi\mu r v$, where μ is the dynamic viscosity of the fluid and r and v are the radius and the drag velocity of the microparticle, respectively. Hence, the drag velocity is linearly related to the saturation magnetization of microparticles with equal diameter, submerged in the same fluid and subjected to the same magnetic field, and is described by $v=mM_s\nabla H/6\pi\mu r$.

Example 13

Hydrophobic Nanoparticles (Ferrofluid) Synthesis 48 g $FeCl_2\cdot 4H_2O$ and 98 g $FeCl_3\cdot 6H_2O$ were dissolved in 250 ml deoxygenated water in a 1 L three neck under $N_2$ atmosphere. The flask was placed into an ice bath whilst ammonium hydroxide (200 ml) added rapidly with vigorous stirring. The solution was kept at 0° C. for 45 min, after which the solution was heated to 85° C. for 1 h, before 30 ml of Oleic acid was added and continued to heat for a further 60 mins. The flask was allowed to cool to room temperature before being transferred to a 600 ml beaker. A magnet was placed next to the beaker to collect the black precipitate, which was washed three times with ethanol (200 ml), after each wash a magnet was placed next to the beaker and the ethanol solution poured to waste. This process was repeated with DI water (200 ml) three times followed by 20% perchloric acid (200 ml) three times, DI water (200 ml) three times and finally ethanol (200 ml) three times. After the last ethanol wash the solution was poured away and hexanes (400 ml was added to the beaker. The black precipitate (iron oxide nanoparticles) was easily dispersed in hexane resulting in a nonaqueous ferrofluid.

Emulsification Using Couette Mixer

Dextran (Affymetrix Mw 60,000-90,000) 25% w/w, SDS 2% w/w solution 60 mL and hexane 20 mL containing dissolved iron oxide nanoparticles are pumped into the couette mixer at different inlet ports. The aqueous phase is pumped at a rate of 0.75 mL/min feeding speed and the organic phase at a rate of 0.25 mL/min. The droplet size was adjusted through variation of the shear rate. The homogenised emulsion was collected in a drying bath (850 mL at 0.5% Triton) under gentle agitation (150-170 rpm) and the emulsion was left to dry for 24 hours. Using a magnet the microparticles were collected on the bottom for 2 h and removed the upper solution. The collected microparticles were washed with 0.5% Triton-100 solution for 2 times to remove residual dextran.

Emulsion/SMP Size Characterization

Images of the emulsion droplets were obtained using a Zeiss microscope with a 60× or 100× objective lens in Differential Imaging Contrast (DIC) mode. SEM Images of the microparticles were obtained using a Hitachi Z-4300 with an accelerating voltage of 15 kV. Optical sizing software (Axiovison 4.8) was used to measure droplet and microparticle size distributions from the obtained images. More than 80 data points were used when measuring size distributions of superparamagnetic particles and emulsion droplets.

BET Surface Area Analysis

All magnetic properties were performed on a Quantum Design, Magnetic properties measurement system, MPMS, Superconducting Quantum Interference Device. Scanning electron microscopy images, SEM, images were taken on a Hitachi S-4300 Scanning electron microscope with accelerating voltage of 15 kV. Iron content was analysed using atomic adsorption.

Microparticles were produced using the ESE method described above, varying the concentration of iron oxide nanoparticles in the hexane phase between 0.1 and 1 mg/ml. The morphology of the microparticles can be seen in FIG. 6, nanoparticle concentrations above at or above 1 mg/ml the microparticles were smooth and spherical, at 0.5 mg/ml the microparticles were dimpled and at 0.1 mg/ml the microparticles had a crumpled morphology. TEM images of cross-sections of the microparticles are shown in FIG. 7. The hollow nature of the dimpled and crumpled particles indicates that the particles were formed through a shell formation and buckling mechanism. The surface area to mass ratio of the microparticles is higher for dimpled and crumpled particles than for spherical particles. In order to confirm this, a colorimetric assay was performed where the biotin-HRP binding capacity per milligram was measured for each of the different microparticle morphologies after streptavidin functionalisation. As shown in FIG. 9, higher binding capacities per milligram of the dimpled and crumpled microparticles demonstrate larger surface area to mass ratio than spherical microparticles. The velocity of the different types of microparticles in a magnetic field was also investigated. The largest diameter (measured as maximum diameter) particles (1.2 µm approx) were isolated through centrifugation for each morphology, and suspended in a well at a varying distance from a bar magnet. The velocities of the different types of microparticles with distance from the bar magnet is shown in FIG. 8. The surface area of superparamagnetic microparticles can be increased by decreasing the diameter of the microparticles, however this also drastically reduces the velocity of the microparticles in a magnetic field. The novel dimpled and crumpled particle morphologies introduced here have a higher surface area to mass ratio than similar sized spherical microparticles, while maintaining large magnetic field velocities due to their large size and solely magnetite composition, making them more suitable for large scale magnetic separation processes where high microparticle surface area and magnetic field velocity are desirable.

It has been shown that the method 200 of the present specification provides that the particle morphology can be tuned by controlling parameters including the drying conditions. As a result of this, the morphology of the microparticles 100 can be tuned to be dimpled or crumpled dramatically increasing the surface area to volume ratio of the micron sized particles, while maintaining a high magnetic moment due to the absence of polymer. In comparison with similar commercially available microparticles Dynal beads produced by Invitrogen, the microparticles 100 show higher magnetisation due to the absence of polymer, have higher surface area than conventional spherical microparticles and, advantageously can be produced without using more complex double emulsion or templating and etching processes. The method can also be used to provide porous or hollow microparticles.

A method 200 and system 1 for the synthesis of microparticles has been described. Microparticles 100 of different morphologies have been provided included crumpled and dimpled microspheres. The crumpled and dimpled microparticles have an advantageous configuration over similar sized spherical microparticles for applications in affinity separations, targeted drug delivery, diagnostics due to their high surface area and magnetic mobility. The microparticles may be superparamagnetic microparticles comprised of superparamagnetic nanoparticles. The microparticles may also comprise other material for example polymer, fluorescent material or an encapsulated drug.

Alternatives types of microparticles may also be provided according to the method and system as described. In particular the crumpled and dimpled microparticles have surface area to volume ratio. The microparticles 100 comprised of superparamagnetic nanoparticles have a high binding capacity and magnetic mobility or separation velocity. Microparticles comprising self-assembled iron-oxide microparticles demonstrate a higher magnetic moment than either the individual nanoparticles or polymer/magnetite composites.

The present specification further provides a method 400 for producing superparamagnetic microspheres 500 which are produced using an emulsion solvent evaporation (ESE) method 400. There are two basic types of ESE; one using direct oil in water (O/W) or water in oil (W/O) emulsions and the second using double W/O/W or O/W/O emulsions.

The preparation of single emulsions consists of two steps; the first step involves the emulsification of the polymer or nanoparticle suspension in a second immiscible phase, with surfactant used to stabilise the droplets, and the second step involves the evaporation of the solvent and the accompanying crystallisation/precipitation of the polymer or nanoparticles.

The preparation of double emulsions is similar to that of single emulsions, but with a second emulsification step where the primary emulsion is emulsified in a third phase. Porous and hollow superparamagnetic microspheres 500 in the size range of 3-10 microns are produced by the ESE method 400.

The formation of double W/O/W emulsions and subsequent hardening of the dissolved material provides for the hollowness and porosity of the microspheres. The methods of preparation of the hollow (FIG. 16) and the porous (FIG. 17) microspheres differ slightly in the types and concentrations of surfactants used to stabilise the emulsions and the concentrations of iron oxide nanoparticles in the oil phase.

Synthesis of porous particles has been described in exemplary methods of examples 6-8 above, FIGS. 17 and 18 show examples of porous particles. Referring to FIG. 1 a 20% w/w dextran 30 mL (Sigma Aldrich Mw 150,000) was pumped into the couette mixer at a rate of 0.75 mL/min, and 10 ml hexane containing 80 mg/ml hydrophobized iron oxide nanoparticles and 5% w/w oleic acid (Fisher Scientific) was pumped into the mixer at a rate of 0.25 mL/min. The rotor speed was adjusted to 150 RPM. The homogenised emulsion was transferred to an evaporation dish containing 800 ml water at 0.5% w/w Triton X-100 (Sigma Aldrich) under gentle agitation. After 24 hours the dried microspheres 500 were collected with a magnet and washed with 0.5% Triton X-100 solution to remove residual dextran The method includes
Using oleic acid—a low HLB surfactant—to stabilise the emulsion produced porous high surface area particles Superparamagnetic microspheres have applications in affinity separations due to the speed, ease, efficiency and inexpensive nature of magnetic separation. The microspheres can be functionalized with receptors such as antibodies that are capable of binding to specific ligands on the target of interest such as cells, proteins and viruses in fermentation broths and culture media. A magnet can then be used to separate the microspheres together with the target of interest. The microparticles previous have been typically composed of iron oxide superparamagnetic nanoparticles for example distributed in a polymer microparticle matrix. Self-assembled iron-oxide microspheres consisting solely of iron oxide nanoparticles demonstrate a higher magnetic moment than either the individual nanoparticles or polymer/magnetite composite microparticles. For magnetophoric affinity separations there is a compromise between increasing the surface area and the magnetic moment of the particles in a magnetic field. For example, by simply functionalising individual nanoparticles (~10 nm) the surface area is increased but the magnetic moment is very low and therefore separation times are extremely slow. On the other hand separation times are faster for assembled microspheres but the surface area of spherical microspheres is reduced compared with nanoparticles (the surface area to volume ratio of spherical microspheres scales with 1/r, where r is the radius of the microsphere) The method 400 provides a way to increase the surface area of microparticles 500 while maintaining high magnetic moment by using large (~10 μm) porous microparticles.

One approach to attain higher surface areas without changing the surface area to volume ratio of the microparticles is to use higher concentrations of spherical microspheres. Smaller microparticles can be used (the surface area to volume ratio of spherical microspheres scales with 1/r, where r is the radius of the microsphere. Alternatively, microparticles with non-spherical morphologies can be used to achieve more favourable combinations of surface area to volume and magnetic mobility that is not possible with spherical microspheres. Porous superparamagnetic Gd20O$_3$ 200 nm microparticles have been previously developed, where the Gd20 O$_3$ was deposited on a gelatine core or in an organic gelatin matrix which was subsequently removed using calcination resulting in hollow and porous spheres. Similar methods reported also require etching of a template core to obtain the necessary porous structure. A double emulsion ESE (as used here) method has also been used to produce hollow polymeric microspheres with magnetite embedded in a polystyrene matrix. The use of higher concentrations of spherical microspheres to achieve a higher surface area is costly and inefficient. Reducing the size of the microspheres significantly reduces the magnetic mobility of the microparticles, which scales with 1/r$^2$. The deposition of nanoparticles onto a gelatin core or matrix and subsequent removal of gelatin by calcination to produce hollow micro spheres is time consuming. While a double emulsion templated method has been used to produce hollow polymer/magnetite composites, these composites contained a lower amount of magnetite than microspheres made purely with magnetite according to the present specification and therefore have a lower magnetic moment.

The method of preparation of porous superparamagnetic microspheres reported here does not require the incorporation of a gelatin or polymer template as the iron oxide nanoparticles self assemble upon drying. Therefore there are a lower number of steps (no templating and etching) in the microparticle production process and the iron oxide content and therefore magnetisation of the microspheres is higher, rendering them more mobile and easier to manipulate in a magnetic field, due the large magnetic mobility of the porous microparticles.

The porous are advantageous from point of view of ease of manufacture, binding capacity and magnetic mobility.

As the previous couette mixer of homogenisation produces a range of droplet sizes, the desired hollow spheres are formed together with smaller denser microspheres and some fragments of large hollow microspheres. The droplet size distribution should be better controlled to solely produce the desired hollow microspheres. The porous microspheres can be developed reproducibly although the exact mechanism of their formation and their internal structure have not been fully characterised. Centrifugation is required to separate the largest size fraction of porous microparticles (10-15 μm).

The surface area of the microspheres is significantly increased when compared to solid microspheres of equal size, while a high magnetic moment is maintained by using large microparticles (as opposed to nanoparticles) and not incorporating a polymer into the microsphere.

The present specification further provides a method 400 for producing superparamagnetic microspheres 500 which are produced using an emulsion solvent evaporation (ESE) method 400. There are two basic types of ESE; one using direct oil in water (O/W) or water in oil (W/O) emulsions and the second using double W/O/W or O/W/O emulsions.

The preparation of single emulsions consists of two steps; the first step involves the emulsification of the polymer or nanoparticle suspension in a second immiscible phase, with surfactant used to stabilise the droplets, and the second step involves the evaporation of the solvent and the accompanying crystallisation/precipitation of the polymer or nanoparticles.

The preparation of double emulsions is similar to that of single emulsions, but with a second emulsification step where the primary emulsion is emulsified in a third phase. Porous and hollow superparamagnetic microspheres 500 in the size range of 3-10 microns are produced by the ESE method 400.

The formation of double W/O/W emulsions and subsequent hardening of the dissolved material provides for the hollowness and porosity of the microspheres. The methods of preparation of the hollow (FIG. 9) and the porous (FIG. 10) microspheres differ slightly in the types and concentrations of surfactants used to stabilise the emulsions and the concentrations of iron oxide nanoparticles in the oil phase.

In one example, a mixture of 8 g dextran (Affymetrix Mw 60,000-90,000) and 0.16 g sodium dodecyl sulfate (Sigma Aldrich) is dissolved in 24 ml deionised water and added to 10 ml hexane containing 100 mg/ml hydrophobized iron oxide nanoparticles in a 50 ml tube.

An emulsion 450 is produced by gently mixing the phases on a rotating wheel for 30 minutes. The premixed emulsion 450 (40 ml is then homogenised in a couette type shear mixer 460, being pumped through at a rate of 1 ml/min with a rotor speed of 175 RPM (residence time approx 30 s). The homogenised emulsion is transferred to an evaporation dish containing 800 ml water at 0.5% w/w Triton X-100 (Sigma Aldrich) under gentle agitation. After 24 hours the dried microspheres 500 are collected with a magnet and washed with 0.5% Triton X-100 solution to remove residual dextran In one example, a mixture of 8 g dextran (Affymetrix Mw 60,000-90,000) is dissolved in 24 ml deionised water and added to 10 ml hexane containing 15 mg/ml hydrophobized iron oxide nanoparticles and 0.7 g oleic acid (Sigma Aldrich) in a 50 ml tube. An emulsion is produced by vigorously hand mixing the emulsion for 1 min followed by gently mixing the phases on a rotating wheel for 1 hour. The premixed emulsion (40 ml) is then homogenised in a couette type shear mixer, being pumped through at a rate of 1 ml/min with a rotor speed of 200 RPM (residence time approx 30 s). The homogenised emulsion was then transferred to an evaporation dish containing 800 ml water at 0.5% w/w Triton x-100 (Sigma Aldrich), under gentle agitation. After 24 hours the dried microspheres were collected with a magnet, washed with 0.5% Triton x-100 solution to remove residual dextran.

Variation of surfactant hydrophilic-lipophilic balance (HLB)

High HLB surfactants similar to SDS—Triton X-100 and Tween 20—were used to stabilise emulsions and yielded spherical, although slightly rough particles Using oleic acid—a low HLB surfactant—to stabilise the emulsion produced porous high surface area particles May be produced as a result of W/O/W emulsions These particles have a high surface area to volume ratio, and have a higher velocity in a magnetic field than using a batch of smaller particles to obtain the same surface area Superparamagnetic microspheres have applications in affinity separations due to the speed, ease, efficiency and inexpensive nature of magnetic separation.

The microspheres can be coated with receptors such as antibodies that are capable of binding to specific ligands on the target of interest such as cells, proteins and viruses in fermentation broths and culture media. A magnet can then be used to separate the microspheres together with the target of interest.

The microparticles previous have been typically composed of iron oxide superparamagnetic nanoparticles for example distributed in a polymer microparticle matrix. Self-assembled iron-oxide microspheres consisting solely of iron oxide nanoparticles demonstrate a higher magnetic moment than either the individual nanoparticles or polymer/magnetite composite microparticles.

For magnetophoric affinity separations there is a compromise between increasing the surface area and the magnetic moment of the particles in a magnetic field. For example, by simply functionalising individual nanoparticles the surface area is increased but the magnetic moment is very low and therefore separation times are very slow. On the other hand separation times are faster for assembled microspheres but the surface area of spherical microspheres is low. The method 400 provides a way to increase the surface area of microparticles 500 while maintaining high magnetic moment by using porous or hollow microparticles.

A straight-forward approach is to use higher concentrations of spherical microspheres to achieve the higher surface area required without changing the surface area to volume ratio of the microparticles. Porous superparamagnetic Gd20O$_3$ 200 nm have been previously developed, where the Gd20 O$_3$ was deposited on a gelatine core or in an organic gelatin matrix which was subsequently removed using calcination resulting in hollow and porous spheres. Similar methods reported also require etching of a template core to obtain the necessary porous structure. A double emulsion ESE (as used here) method has also been used to produce hollow polymeric microspheres with magnetite embedded in a polystyrene matrix.

The use of higher concentrations of spherical microspheres to achieve a higher surface area is costly and inefficient. The deposition of nanoparticles onto a gelatin core or matrix and subsequent removal of gelatin by calcination to produce hollow micro spheres is time consuming. While a double emulsion ESE method has been used to produce hollow polymer/magnetite composites, these composites contain a lower amount of magnetite than microspheres made purely with magnetite according to the present specification and therefore have a lower magnetic moment.

The method of preparation of the hollow and porous superparamagnetic microspheres reported here does not require the incorporation of a gelatin or polymer template as the iron oxide nanoparticles self assemble upon drying. Therefore there are a lower number of steps (no templating and etching) in the microsphere production process and the iron oxide content and magnetisation of the microspheres is higher, rendering them more mobile and easier to manipulate in a magnetic field.

Although they can be synthesised reproducibly, hollow microspheres form above a certain threshold size below which dense homogeneous microspheres form. At droplet sizes well above this threshold the formed hollow microspheres are structurally unstable and break apart. As the current couette mixer of homogenisation produces a range of droplet sizes, the desired hollow spheres are formed together with smaller denser microspheres and some fragments of large hollow microspheres. The droplet size distribution should be better controlled to solely produce the desired hollow microspheres. The porous microspheres can be developed reproducibly although the exact mechanism of their formation and their internal structure have not been fully characterised. In both cases the available surface area and velocity in a magnetic field have not been characterised.

The surface area of the microspheres is significantly increased when compared to solid microspheres of equal size, while a high magnetic moment is maintained by using large microparticles (as opposed to nanoparticles) and not incorporating a polymer into the microsphere.

ADVANTAGES AND APPLICATIONS

The system 1 and method 200 of the present specification enables the high throughput production of emulsions and precise control over emulsification and drying steps to reproducibly synthesise uniformly sized particles with the required morphology on a large scale. The specification further provides shear device 10. The use of separate inlet ports according to the shear device 10 of the system 1 of the present specification addresses the problems mentioned in connection with previous methods for example, when separate inlets are used for the different phases, emulsification occurs within the shear device, and therefore no premixing is required.

Phase separation of the premix is no longer an issue with the separate inlet setup. Therefore the system can be scaled up and the production time is limited only by the capacity of the individual continuous and dispersed phase reservoirs, in comparison with previous methods where there were problems associated with premix phase separation limiting the batch size. The use of separate ports for the dispersed and continuous phases allows the dispersed phase volume fraction to be precisely controlled over the entire course of production, resulting in precise control over droplet size and size distribution.

The use of an enclosed drying bath with precise control over bath temperature, mixing rate, and head space vapour pressure ensures that microparticles are formed with the desired morphology.

In the system and method of the present specification, the use of separate ports, enabling scale up of emulsion/superparamagnetic particle synthesis, is advantageous over approaches that have been used previously. The provision of a scalable method is advantageous for the production of microparticles on a commercial scale providing for increased reliability of the method and decreased costs. Further the system and method of the present specification allow large scale synthesis of uniform emulsions or the large scale emulsion templated synthesis of uniform polymeric microspheres.

Superparamagnetic microparticles have applications in targeted drug delivery, diagnosis, and are widely used in affinity separations due to the speed, ease, efficiency and inexpensive nature of magnetic separation. The microparticles are typically composed of iron oxide superparamagnetic nanoparticles either distributed in a polymer microparticles matrix, or self-assembled to form a tightly packed superparamagnetic microparticle. Self-assembled iron-oxide microparticles demonstrate a higher magnetic moment than either the individual nanoparticles or polymer/magnetite composites. Emulsion templated self-assembly of superparamagnetic nanoparticles may be used to produce for example, spherical superparamagnetic microspheres.

Superparamagnetic microparticles are extensively used in the purification of biomolecules due to the speed and ease of magnetic separation. It is desirable that the microparticles used in biological affinity separations have both high surface area and high magnetic mobility to facilitate a high binding capacity of target biomolecules and their rapid removal from solution, respectively. Scaling laws for conventional spherical superparamagnetic microparticles are such that increasing the microparticle specific surface area results in a significant decrease in the magnetic mobility. More favorable combinations of these key parameters can be found if alternative microparticle morphologies are developed for use in affinity separations. Emulsion-templated self-assembly of iron oxide nanoparticles into microparticle using oil-in-water emulsions was carried out using a modified Couette shear mixer as described with separate inlet ports for the oil and aqueous phases, enabling high throughput microparticle synthesis. By controlling the dissolved nanoparticle concentration and nanoparticle surface activity at the droplet interfaces, the resulting microparticles were tuned to spherical, dimpled, or crumpled morphologies. The specific binding capacity and magnetic mobility of each type of microparticle were measured by a peroxidase-based colorimetric assay and by their magnetic field-induced motion in a viscous fluid, respectively. Superparamagnetic microparticles with dimpled and crumpled morphologies were found to have higher specific binding capacities compared to spherical microparticles, while maintaining high magnetic field velocities due to their high iron oxide content. Superparamagnetic microparticles with these novel morphologies would make excellent tools for affinity-based bioseparations where binding capacity and magnetic mobility are key factors.

It is desirable that SMPs used in biological affinity separations have both high surface area and high magnetic mobility. The large surface areas provide, when functionalized with the appropriate ligands, a higher binding capacity, and therefore a lower mass of SMPs is required to achieve high analyte recovery. High magnetic mobilities enable fast separation of SMPs and reduce the time required to separate the beads from the supernatant after binding occurs.

Although reducing the diameter of spherical SMPs increases the surface area per mass, the magnetic mobility of the SMPs is reduced significantly, as it is proportional to the square of the microparticle radius. A solution to this limitation is provided by changing the SMP morphology from spherical to either hollow, porous, or buckled morphologies. A number of efforts have been made in this respect, with the primary focus on the use of the development of hollow SMPs for drug encapsulation for targeted delivery.

In previous methods nanoparticles were deposited on a gelatine core or in an organic gelatin matrix which was subsequently removed using calcination resulting in hollow and porous spheres. In a similar previously used method etching of a template core was required to obtain the necessary porous structure. In another method double emulsions have also been used to produce polymeric microspheres with magnetite embedded in a polystyrene matrix.

In comparison with the prior art there are advantageously fewer steps in the microsphere production process of the present specification. Further, advantageously the iron oxide content and magnetisation of the microspheres is higher, resulting in microparticles with high magnetic mobilities which are easier to manipulate in a magnetic field.

The crumpled microparticles have a magnetic mobility 6 times lower than spherical particles, but a binding capacity 6-7 times higher. A spherical particle which had the same binding capacity per unit mass of beads as the crumpled particle, it would be about 150 to 200 nm, and would have a mobility about 30 to 40 times lower than that spherical bead, or 5 times lower than the crumpled particle that has the same binding capacity as it.

Advantageously in comparison with previous methods, the method of the present specification are simplified. In previous methods there is often an extra processing step in the form of removing the original template onto which the polymer-magnetite was deposited. The direct emulsion method of the present specification does not require the use of a template, an etching step, or the incorporation of a polymer.

Further the particles generated using the methods of the present specification have advantages in comparison with particles produced using the aforementioned prior techniques such as for example microparticles having magnetite embedded in a polymer matrix. For such particles the incorporation of the non-magnetic polymer reduces the magnetic moment and therefore magnetic separation velocity of these particles The method and system provide for large scale particle production. Microparticles may be produced in batches. In one prior art approach input was provided via a single channel. Here, the inputs are provided in a continuous stream Advantageously, the emulsion templated self assembly method of the present specification an improved method for production of microparticles. The method provides for production microparticles of various size and morphology, as required. Advantageously, the method provides for production of a batch of particles of reduced size distribution/uniform particle size and accordingly improved % CV in comparison with the previous methods. Advantageously the method provides for production of microparticles of different morphologies including spherical, crumpled, dimpled, porous and hollow, as required. The method includes a relatively small number of steps including the following: preparing an emulsion of an organic solvent containing dispersed metal oxide nanoparticles, for example, iron oxide nanoparticles at the selected concentration in an aqueous continuous phase, and then allowed to dry.

In comparison with prior art approaches, the present method does not require the use of a pre-mixed emulsion being provided to a shear device for emulsification. Rather the separate phases are provided to the shear device. There is no premixing of the emulsion required and accordingly phase separation of the premixed emulsion does not occur and is not an issue. Throughput of the system of the present specification and the method of production of the present specification is accordingly limited not by factors such as separation of the pre-mixed emulsion. Therefore it is possible for the system of the present specification to be scaled up. The production time is limited only by the capacity of the individual continuous and dispersed phase reservoirs. While spray drying may be used to dry particles, it is noted that the time-scales of microparticle formation differ greatly between spray drying and emulsion driven nanoparticle self-assembly.

The Couette shear device 10 having a cylindrical rotor and stator type arrangement is different to prior art devices, which may for example include flat plate or impellor or impellor and screen mesh device. Advantageously, the shearing force applied to the emulsion and droplets is uniform throughout the Couette shear device 10 and is controllable including by control of rotation speed of the rotor. In contrast in a flat plate device the shearing force depends on the rotation speed of the mixer and the radial distance from the centre of the plate i.e. it is not constant in the flat plate device for a particular rotation speed. As the final droplet size is proportional to the shearing force, it is desirable to have this force uniform, as in our setup. The arrangement of the device of the invention provides improved uniformity and control of the shearing force.

The method of the specification provides for example for use of either nanoparticles alone dissolved in an organic solvent or a nanoparticle-polymer mixture. There is no further step for example incorporation of nanoparticles in a polymer melt in an organic solvent for the dispersed phase. The method provides that, superparamagnetic nanoparticles may comprise substantially 100% of the microparticle, conferring high magnetic mobilities to the microparticles. Microparticle morphology may be tailored by the method provided to give high surface area to volume ratios.

The use of a shear device having separate inlets for the phases, resulting in more controlled flowrates, and therefore more controlled dispersed phase volume fraction—critical in controlling droplet size and uniformity. The method provided has a low coefficient of variance without the further step of for example centrifugation.

According to the present specification there is provided a method and system for the production of microparticles. The method and system may be adapted flexibly to enable production of microparticles of controlled size, morphology/ surface area and tuneable magnetisation, as required. By control of morphology and surface area it is possible to provide a microparticle of relatively high binding capacity relative to similar sized (similar radius) particles of the prior art. By control of magnetisation it is possible to provide microparticles of relatively high magnetic mobility in comparison with similar sized microparticles of the prior art.

The method and system further advantageously provide for improved particle size distribution or more uniform particle size distribution. The method is therefore of improved efficiency and there is reduced waste and loss.

In effect, the method and system may be used to produce microparticles of uniform size and monodispersity. Particles produced by the method and system may have CV ratio preferably of the order of <25%. The method and system of the present specification advantageously provides a relatively simplified method for production of microparticles. Further the method of production of microparticles is highly reproducible.

As described previously emulsification occurs in the shear device in the gap between the rotor and stator. The gap size may be controlled to provide the required results. The gap size is preferably of the order of 100 mn. The system also provides for high control of the speed of rotation. The system also provides for relative high speeds of rotation.

The spherical, crumpled, dimpled, porous and hollow microparticle morphologies are advantageous for various applications. Microparticles of different sizes may be used preferentially for different particular applications. Microparticles of different magnetic mobility may be preferred for different applications. Microparticles of different binding capacity may be preferred for different applications. The method and system provide the ability to produce a batch of particles of a particular size in the range of from substantially.

For example, in contrast MRI applications, magnetic particles may be provided according to the present specification having different magnetisation. Such would allow for multiplex detection via MRI of different colours. For example, according to the method and system described, different nanoparticles for example Iron nanoparticles such as $Fe_2O_3$ and $Fe_3O_4$ may be provided to produce tuneable magnetisation.

The method provides tuneable magnetisation via selection of nanoparticles. Particles with tuneable magnetisation also have application for use in magnetophoresis.

Functionalised superparamagnetic microparticles are often used in laboratory setting for the separation and purification of biomolecules such as nucleic acids and proteins.

Advantageously, in comparison with previous approaches the present method does not require centrifugal separation. No centrifugal separation is required for example for spherical microparticles of the order of 350 nm.

The crumpled particles described in Example 1 are comprised solely of iron oxide, advantageously resulting in higher mobility than for example, previous polymer-iron oxide composite particles.

The parameters determining particle morphology (i.e. spherical, dimpled and crumpled and porous) are highly controllable and reproducible. The surface area/binding capacity of the different types of particles has been accurately measured times using a colorimetric biotin-HRP and -Avidin assay The method of preparation of the porous superparamagnetic microspheres of the present specification does not require the incorporation of a polymer as the iron oxide nanoparticles self-assemble upon drying.

As noted above different microparticles of controlled morphology and size, surface area and magnetisation may be used for different applications. Different microparticles may be used in different diverse applications including diagnostics where for example microparticles may be used to provide separation of an analyte automatically in a handheld strip diagnostic device. Microparticles suitable for large scale separations in the range of substantially 5-500 L may be provided. Large scale separation advantageously provides for a low cost and efficient separation. Constraints of the prior art addressed by the present application include time requirement or speed of the separation and magnetic field requirements. However, the method and the system of the invention advantageously provides for production of microparticles of relatively high surface area accordingly with increased binding capacity relative to similar sized particles of the prior art and further at the same time provide for particles of high magnetic mobility. Such particles may therefore be used for large scale separations of relative high speed without onerous requirements for magnetic field allowing a high throughput in separations for example of the order of 10 k analytes per day.

Other applications of magnetic particles provided by the method and system of the present application include therapeutic and in vivo imaging.

The invention claimed is:

1. A method of producing microparticles using an emulsion based synthesis route, the method comprising:
(i) providing a first fluid phase and a second fluid phase, wherein the first fluid phase is a continuous phase and the second fluid phase is a dispersed phase comprising a dispersed material, wherein the continuous phase is immiscible with the dispersed phase;

(ii) providing a shear device having a first inlet for the first continuous phase and a separate second inlet for the second dispersed phase, the shear device having a rotor configured to revolve inside a stationary stator and an annular gap between the rotor and stator in which emulsification occurs;

(iii) mixing the first continuous phase and the second dispersed phase in the presence of a surfactant in the shear device to form an emulsion of droplets of controllable size and uniformity of droplet size distribution, wherein the mixing step comprises an emulsifying step where the second dispersed phase is emulsified into the first continuous fluid phase in the shear device;

(iv) controlling a volume fraction of the second dispersed phase during the mixing step by controlling the flow rate of the first continuous phase at the first inlet and the second dispersed phase at the second inlet; and (v) drying the emulsion to form microparticles of controllable size and uniformity of particle size distribution, and wherein the microparticles may comprise spherical, crumpled, dimpled, porous or hollow microparticles morphology.

2. The method of claim 1 wherein the droplets are of less than 50 micron diameter and the microparticles formed are of less than 15 micron diameter.

3. The method of claim 1, wherein the microparticles formed have a size distribution having a % CV diameter of the order of 25% CV or less.

4. The method of claim 1 further comprising
controlling microparticle morphology to provide the microparticles of spherical, crumpled, dimpled, porous or hollow morphology.

5. The method of claim 1, wherein droplet size is less than 20 microns.

6. The method of claim 1, wherein microparticle size is in the range of 200 nm-1 micron.

7. The method of claim 1 wherein the dispersed material comprises nanoparticles.

8. The method of claim 1 wherein the dispersed material comprises superparamagnetic nanoparticles.

9. The method of claim 7 wherein the nanoparticles are metal oxide nanoparticles.

10. The method of claim 8 further comprising controlling magnetization of the microparticles.

11. The method of claim 10 wherein the magnetization of the microparticles is controlled by controlling the concentration of iron oxide $Fe_2O_3$ and/or $Fe_3O_4$ nanoparticles in the dispersed phase in the range of 0.1-200 mg/mL.

12. The method of claim 10 wherein the magnetization of the microparticles is controllable substantially in the range of 20-110 emU/g.

13. The method of claim 1 further comprising controlling the shear device to control droplet size and uniformity of size distribution and controlling selection of continuous and dispersed phases.

14. The method of claim 1 further comprising controlling: the shear rate and/or dispersed phase volume fraction and/or continuous phase viscosity and/or surfactant concentration and/or the viscosity ratio between phases, and/or the dispersed phase viscosity, to control microparticle size and uniformity of the size distribution of the microparticles.

15. A shear mixing device for mixing a first fluid phase and a second fluid phase, the device comprising:

first and second inlet ports for the first fluid phase and the second fluid phase respectively, the first and second inlet ports being configured for connection to continuous and dispersed phase reservoirs;

a rotor configured to rotate inside a stationary stator at a rate of rotation controllable substantially up to 2000 rpm, the rotor and the stationary stator being arranged such that a gap on the order of 100 microns is provided there between and such that in use as the rotor rotates emulsification of the dispersed phase into the continuous phase occurs inside the shear device in said gap to form an emulsion comprising emulsion droplets, wherein the radius of the rotor and gap size between the rotor and the stationary stator are optimized to minimize emulsion droplet size distribution;

flow rate control means for controlling the flow rate of the continuous phase and the flow rate of the dispersed phase into the shear device, and shear control means for controlling the shear rate and/or rotation of the rotor; and control means for controlling a volume fraction of the dispersed phase by controlling the relative flow rates of the continuous phase and the dispersed phase into the shear device.

* * * * *